United States Patent
Shibutani et al.

(10) Patent No.: US 11,213,202 B2
(45) Date of Patent: Jan. 4, 2022

(54) OPHTHALMOLOGIC APPARATUS AND METHOD FOR CONTROLLING THE SAME

(71) Applicant: TOPCON CORPORATION, Tokyo (JP)

(72) Inventors: Masahiro Shibutani, Kawaguchi (JP); Tatsuo Yamaguchi, Warabi (JP); Toshihiro Mino, Warabi (JP); Ryoichi Hirose, Itabashi-ku (JP)

(73) Assignee: TOPCON CORPORATION, Tokyo (JP)

( * ) Notice: Subject to any disclaimer, the term of this patent is extended or adjusted under 35 U.S.C. 154(b) by 281 days.

(21) Appl. No.: 16/583,319

(22) Filed: Sep. 26, 2019

(65) Prior Publication Data

US 2020/0015675 A1 Jan. 16, 2020

Related U.S. Application Data

(63) Continuation of application No. PCT/JP2018/021305, filed on Jun. 4, 2018.

(30) Foreign Application Priority Data

Jun. 26, 2017 (JP) .............................. JP2017-123877

(51) Int. Cl.
*A61B 3/12* (2006.01)
*A61B 3/10* (2006.01)
*A61B 3/14* (2006.01)

(52) U.S. Cl.
CPC ............ *A61B 3/1225* (2013.01); *A61B 3/102* (2013.01); *A61B 3/14* (2013.01)

(58) Field of Classification Search
CPC ......... A61B 3/1225; A61B 3/102; A61B 3/14; A61B 3/1025; A61B 3/12

(Continued)

(56) References Cited

U.S. PATENT DOCUMENTS

2010/0110171 A1 5/2010 Satake
2011/0267580 A1 11/2011 Nakajima et al.
(Continued)

FOREIGN PATENT DOCUMENTS

JP 2010-012109 A 1/2010
JP 2010-110392 A 5/2010
(Continued)

OTHER PUBLICATIONS

International Search Report and Written Opinion dated Aug. 21, 2018 for PCT/JP2018/021305 filed on Jun. 4, 2018, 8 pages including English Translation of the International Search Report.
(Continued)

*Primary Examiner* — Mohammed A Hasan
(74) *Attorney, Agent, or Firm* — Xsensus LLP

(57) ABSTRACT

An ophthalmologic apparatus includes an SLO system, a projection system, a first image former, a second image former, a displacement processor, and a controller. The SLO system is configured to scan a target eye with first light deflected by an first optical scanner. The projection system is configured to project second light deflected by an second optical scanner onto the target eye. The first image former is configured to form a first image of the target eye based on a scan result of a first scan region using the first optical scanner. The second image former is configured to form a second image of the target eye based on a scan result of a second scan region using the first optical scanner, the second scan region being narrower than the first scan region. The displacement processor is configured to calculate a displacement between a partial image in the first image and the second image, the partial image corresponding to the second image. The controller is configured to control the second optical scanner based on the displacement.

12 Claims, 16 Drawing Sheets

(58) Field of Classification Search
 USPC .......................................................... 351/206
 See application file for complete search history.

(56) References Cited

U.S. PATENT DOCUMENTS

| | | | | |
|---|---|---|---|---|
| 2015/0150449 | A1* | 6/2015 | Matsumoto | A61B 3/14 |
| | | | | 351/206 |
| 2016/0038023 | A1* | 2/2016 | Endo | A61B 3/102 |
| | | | | 351/206 |
| 2016/0198940 | A1 | 7/2016 | Shibutani et al. | |
| 2018/0116502 | A1* | 5/2018 | Ishinabe | A61B 3/12 |

FOREIGN PATENT DOCUMENTS

| | | |
|---|---|---|
| JP | 2011-135933 A | 7/2011 |
| JP | 2011-229835 A | 11/2011 |
| JP | 2015-043898 A | 3/2015 |
| JP | 2016-041222 A | 3/2016 |
| JP | 2016-063955 A | 4/2016 |
| JP | 2017-029483 A | 2/2017 |
| JP | 2017-046975 A | 3/2017 |

OTHER PUBLICATIONS

Nemoto et al., "Retrieving large multidimensional data using phase-only correlation", DEIM Forum 2011 D6-1, 8 pages.

\* cited by examiner

OPHTHALMOLOGIC APPARATUS AND METHOD FOR CONTROLLING THE SAME

CROSS-REFERENCE TO RELATED APPLICATIONS

The present application is a continuation application of International Patent Application No. PCT/JP2018/021305, filed Jun. 4, 2018, which claims priority to Japanese Patent Application No. 2017-123877, filed Jun. 26, 2017. The contents of these applications are incorporated herein by reference in their entirety.

FIELD

The disclose relates to an ophthalmologic apparatus and a method for controlling the same.

BACKGROUND

Examples of ophthalmologic apparatus (ophthalmic device) for photographing a target eye (subject's eye, patient's eye) include an apparatus using optical coherence tomography (OCT), a fundus camera, a scanning laser ophthalmoscope (SLO), a slit lamp, and the like. Among them, OCT has been drawing attention. OCT forms an image representing the surface morphology, interior morphology, or the like of the target eye using light beam from a laser light source or the like. Unlike X-ray computed tomography (CT), OCT is not invasive on the human body, and therefore is expected to be applied to the medical field or the biological field, in particular. For example, in the field of ophthalmology, apparatuses have been put to practical use for forming images of an anterior segment or the like of the target eye or measuring the intraocular distance.

For the ophthalmologic apparatuses, tracking is an important technique to obtain a high-definition image regardless of the eye movement of the target eye. Here, tracking is to move an optical system of apparatus according to the movement of the target eye. To perform tracking, alignment and focusing are performed in advance. In other words, tracking is a function of maintaining a suitable positional relationship in which alignment and focusing are matched by causing the position or the like of the optical system of apparatus to follow the eye movement. Various types of methods relating to such eye tracking are suggested.

For example, Japanese Unexamined Patent Application Publication No. 2010-012109 discloses an ophthalmologic apparatus that acquires a base image of a fundus and a target image of the fundus using an SLO optical system, obtains differences (displacement amounts) between a plurality of target regions in each image, and performs tracking so that the sum of the obtained differences is minimized.

For example, Japanese Unexamined Patent Application Publication No. 2015-043898 discloses an ophthalmologic apparatus that acquires a base image of a fundus and a target image of the fundus using a fundus camera, performs a phase-only correlation processing on the base image and the target image to obtain a minute displacement amount, and performs tracking based on the obtained displacement amount.

SUMMARY

One aspect of embodiments is an ophthalmologic apparatus including: an SLO system including a first optical scanner deflecting first light, and configured to scan a target eye with the first light deflected by the first optical scanner; a projection system including a second optical scanner deflecting second light, and configured to project the second light deflected by the second optical scanner onto the target eye; a first image former configured to form a first image of the target eye based on a scan result of a first scan region using the first optical scanner; a second image former configured to form a second image of the target eye based on a scan result of a second scan region using the first optical scanner, the second scan region being narrower than the first scan region; a displacement processor configured to calculate a displacement between a partial image in the first image and the second image, the partial image corresponding to the second image; and a controller configured to control the second optical scanner based on the displacement calculated by the displacement processor.

Another aspect of the embodiments is a method for controlling an ophthalmologic apparatus, the ophthalmologic apparatus including: an SLO system including a first optical scanner deflecting first light, and configured to scan a target eye with the first light deflected by the first optical scanner; and a projection system including a second optical scanner deflecting second light, and configured to project the second light deflected by the second optical scanner onto the target eye, the method including: a first image forming step of forming a first image of the target eye based on a scan result of a first scan region using the first optical scanner; a second image forming step of forming a second image of the target eye based on a scan result of a second scan region using the first optical scanner, the second scan region being narrower than the first scan region; a displacement processing step of calculating a displacement between a partial image in the first image and the second image, the partial image corresponding to the second image; and a control step of controlling the second optical scanner based on the displacement.

DETAILED DESCRIPTION

Figure 1:
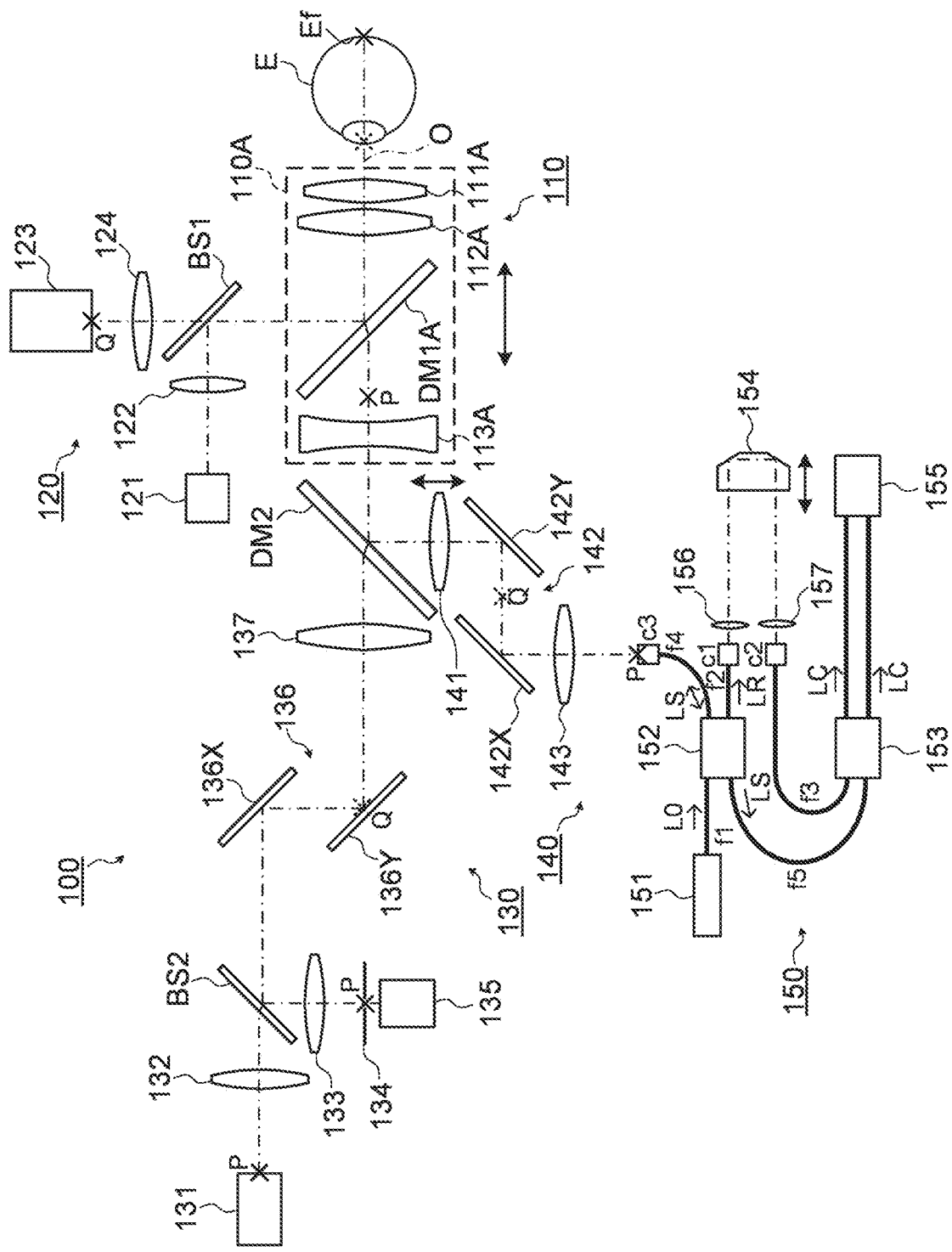
FIG. 1 is a schematic diagram illustrating an example of the configuration of an optical system of an ophthalmologic apparatus according to embodiments.

In the method known to the inventors, it may take time to acquire the target image and to calculate displacement amount, and tracking control may not be able to catch up with the eye movement during that time.

For example, in the method disclosed in Japanese Unexamined Patent Application Publication No. 2010-012109, the target image of the same size as the base image is acquired using the SLO optical system. Thereby, it takes time to scan the fundus, and sometimes the position of the optical system of apparatus or the like cannot follow the eye movement during that time.

On the other hand, for example, in the method disclosed in Japanese Unexamined Patent Application Publication No. 2015-043898, the target image can be acquired in a short time. Thereby, the position of the optical system of apparatus or the like can follow the eye movement with high accuracy. However, it takes time to perform phase-only correlation processing for specifying a minute displacement amount. Thereby, sometimes the position of the optical system of apparatus or the like cannot follow the eye movement during that time.

According to some embodiments of the present invention, an ophthalmologic apparatus and a method for controlling the same capable of performing tracking control with high-speed and high-precision even when an image is acquired using an SLO optical system can be provided.

Referring now to the drawings, exemplary embodiments of an ophthalmologic apparatus and a method for controlling the ophthalmologic apparatus according to the present invention are described below. Any of the contents of the documents cited in the present specification and arbitrary known techniques may be applied to the embodiments below.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

An ophthalmologic apparatus according to the embodiments include an SLO system as a fundus observation system (imaging system). The ophthalmologic apparatus causes a projection position in a target eye of light projected by a projection system to follow the eye movement, by controlling an optical scanner of the projection system based on an image (fundus image) of the target eye (subject's eye, patient's eye) acquired using the SLO system. Example of the projection system include an OCT system, a laser irradiation system, and the like. The OCT system includes an optical scanner and an interference optical system. The interference optical system splits light from an OCT light source into measurement light and reference light, irradiates the target eye with the measurement light, makes returning light of the measurement light from the target eye (fundus) and the reference light having traveled through a reference optical path interfere with each other to generate interference light, and detects the interference light. In the OCT system, the measurement light is deflected by the optical scanner. The laser irradiation system includes an optical scanner and an irradiation optical system. The irradiation optical system is an optical system guiding laser light from a laser light source to the target eye. In the laser irradiation system, the laser light is deflected by the optical scanner.

In the following description, the left/right direction viewed from a subject is regarded as the X direction, the up/down direction is regarded as the Y direction, and the depth direction of an optical system viewed from the subject is regarded as the Z direction.

[Optical System]

Figure 2:
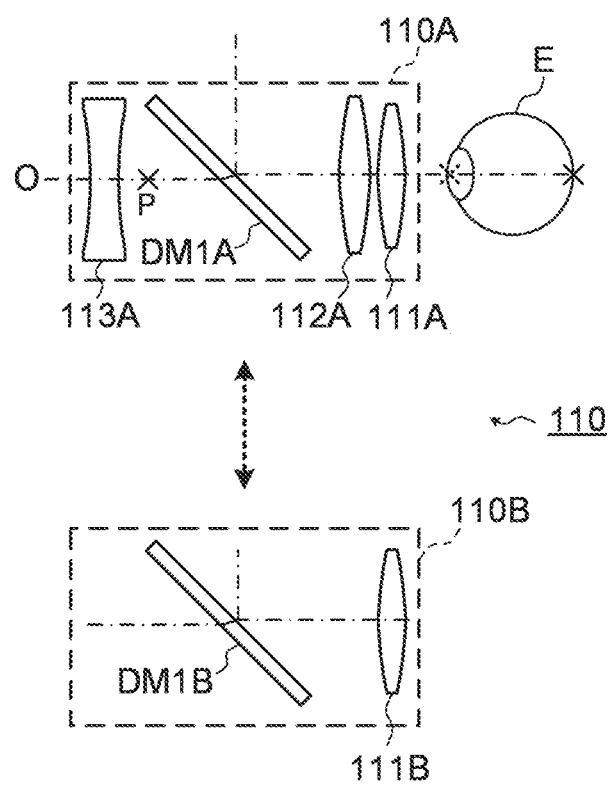
FIG. 2 is a schematic diagram illustrating an example of the configuration of an optical system of the ophthalmologic apparatus according to the embodiments.
Figure 3:
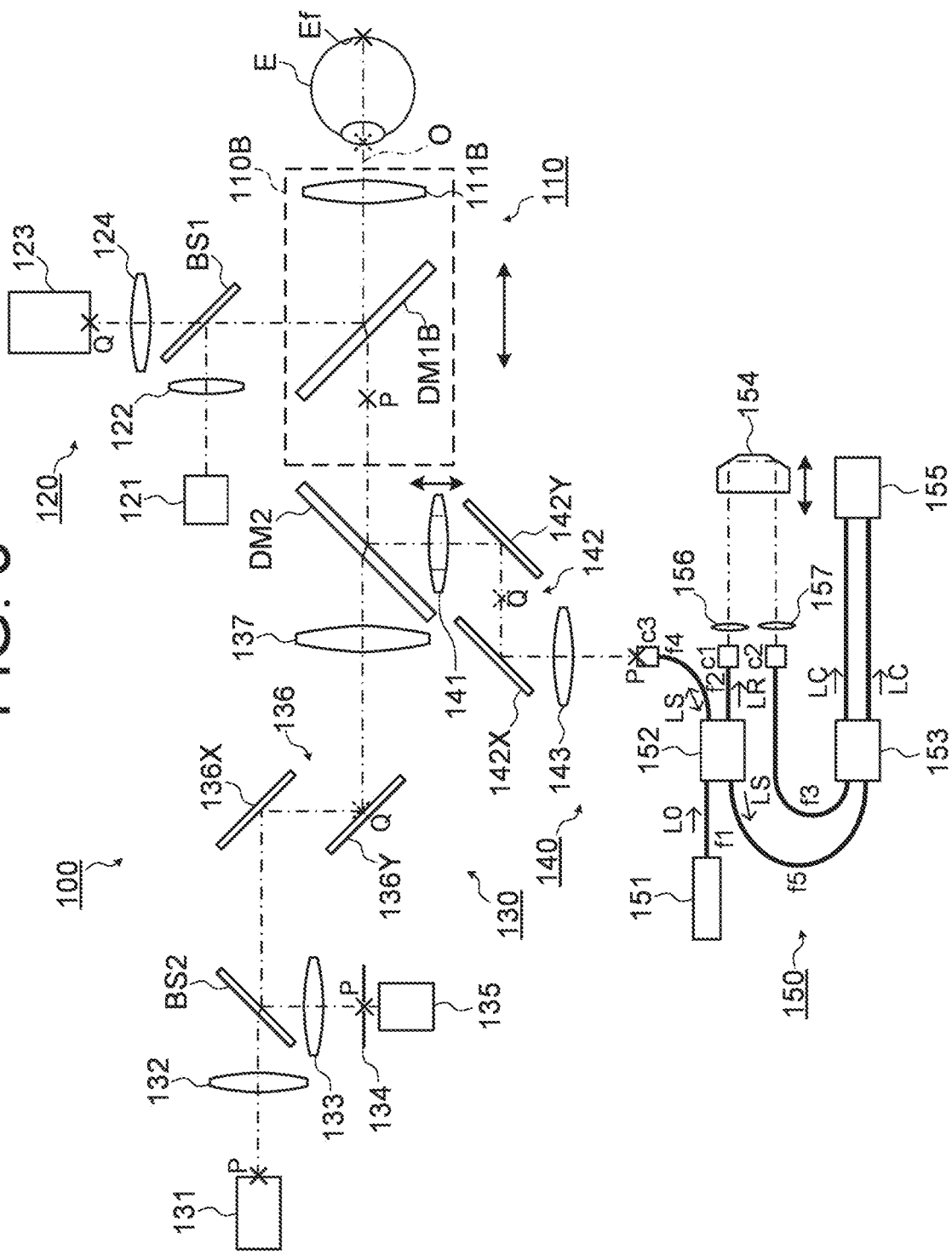
FIG. 3 is a schematic diagram illustrating an example of the configuration of an optical system of the ophthalmologic apparatus according to the embodiments.

FIGS. 1 to 3 illustrate examples of the configuration of the optical system of the ophthalmologic apparatus according to the embodiments. The ophthalmologic apparatus according to the embodiments can acquire an image of a subject's eye in the range corresponding to the photographing (imaging) mode. In the embodiments, the photographing modes include a wide-angle photographing mode for photographing the subject's eye E in a first range (e.g., the angle of view of 100 degrees) and a high magnification photographing mode for photographing the subject's eye E in a second range (e.g., the angle of view of 50 degrees) which is narrower than the first range. The ophthalmologic apparatus can selectively arrange one of objective lens units corresponding to the photographing modes on an optical axis of the optical system.

FIG. 1 shows an example of the configuration of the optical system of the ophthalmologic apparatus when the wide-angle photographing mode is set. FIG. 2 shows an example of the configuration of the objective lens system that can be switched according to the photographing mode. In FIG. 2, like reference numerals designate like parts as in FIG. 1. The same description may not be repeated. FIG. 3 shows an example of the configuration of the optical system of the ophthalmologic apparatus when the high magnification photographing mode is set. In FIG. 3, like reference numerals designate like parts as in FIG. 1 or FIG. 2. The same description may not be repeated. In FIGS. 1 and 3, a position optically conjugate with the fundus Ef of the subject's eye E is illustrated as a fundus conjugate position P, and a position optically conjugate with the pupil of the subject's eye E is illustrated as a pupil conjugate position Q.

An optical system 100 includes a projection system that projects light onto the subject's eye E via an objective lens system 110 and a light receiving system that receives returning light of the light projected onto the subject's eye E by the projection system via the objective lens system 110. The ophthalmologic apparatus forms an image based on the light receiving result obtained by the light receiving system. The ophthalmologic apparatus according to the embodiments can form an SLO image and an OCT image. Such optical system 100 includes an SLO optical system 130 and an OCT optical system 140. The SLO optical system 130 includes an SLO projection system and an SLO light receiving system. The OCT optical system 140 includes an OCT projection system and an OCT light receiving system. It should be noted that the projection system of the optical system 100 may include the laser irradiation system described above in addition to the SLO optical system 130 and the OCT optical system 140. Further, the projection system of the optical system 100 may include the laser irradiation system instead of the OCT optical system 140.

The ophthalmologic apparatus includes an anterior segment photographing system (anterior segment observation system) 120 for photographing the anterior segment of the subject's eye. The optical system 100 is movable with the objective lens system 110 and the anterior segment photographing system 120 in the X direction, the Y direction, and the Z direction by means of a movement mechanism (not illustrated, movement mechanism 100D described later). The movement mechanism moves the optical system 100 etc. based on an anterior segment image of the subject's eye E obtained using the anterior segment photographing system 120, thereby the ophthalmologic apparatus can perform alignment for the position matching of the optical system 100 with respect to the subject's eye E. Hereinafter, cases in which the optical system 100 includes the objective lens system 110 and the anterior segment photographing system 120 will be described. However, the optical system 100 may not include these.

(Objective Lens System)

The ophthalmologic apparatus can arrange objective lens unit corresponding to the photographing mode on an optical axis O of the optical system 100.

The objective lens system 110 includes an objective lens unit 110A and an objective lens unit 110B (see FIG. 2). For example, the objective lens units 110A and 110B can be selectively arranged on the optical axis O by manually using a known rotating mechanism or a known sliding mechanism. In the wide-angle photographing mode, the objective lens unit 110A is arranged so that its optical axis coincides with the optical axis O of the optical system 100 (FIG. 1). In the high magnification photographing mode, the objective lens unit 110B is arranged so that its optical axis coincides with the optical axis O (FIG. 3).

The objective lens system 110A includes two or more lenses. A dichroic mirror DM1A is arranged between (among) the two or more lenses. For example, the objective lens unit 110A may be a lens unit (Nagler type) including a convex lens 111A, a convex lens 112A, and a concave lens 113A. The convex lenses 111A and 112A, and the concave lens 113A are arranged in this order from the subject's eye E side. Between the convex lens 112A and the concave lens 113A, the dichroic mirror DM1A is disposed. The dichroic mirror DM1A is an optical path coupling member to couple an optical path of the anterior segment photographing system 120 with both of an optical path of the SLO optical system 130 and an optical path of the OCT optical system 140 in the wide-angle photographing mode. A position (fundus conjugate position) P or its vicinity optically conjugate with the fundus (retina) is disposed between the dichroic mirror DM1A and the concave lens 113A. The objective lens unit 110A may include the dichroic mirror DM1A.

The dichroic mirror DM1A transmits light (SLO light) from the SLO optical system 130, returning light of the SLO light from the subject's eye E, light (OCT light, measurement light) from the OCT optical system 140, and returning light of the OCT light from the subject's eye E. The dichroic mirror DM1A reflects light from the anterior segment photographing system 120 toward the subject's eye E, and reflects returning light from the subject's eye E toward the anterior segment photographing system 120.

The objective lens unit 110B includes at least one lens. A dichroic mirror DM1B is provided on the light source (SLO light source and OCT light source) side with respect to the at least one lens. For example, the objective lens unit 110B may include a convex lens 111B. The dichroic mirror DM1B is an optical path coupling member to couple the optical path of the anterior segment photographing system 120 with both of the optical path of the SLO optical system 130 and the optical path of the OCT optical system 140 in the high magnification photographing mode. The objective lens unit 110B may include the dichroic mirror DM1B.

Similar to the dichroic mirror DM1A, the dichroic mirror DM1B transmits the light (SLO light) from the SLO optical system 130, the returning light of the SLO light from the subject's eye E, the light (OCT light, measurement light) from the OCT optical system 140, and the returning light of the OCT light from the subject's eye E. Further, the dichroic mirror DM1B reflects the light from the anterior segment photographing system 120 toward the subject's eye E, and reflects the returning light from the subject's eye E toward the anterior segment photographing system 120. A position of the dichroic mirror DM1B on the optical axis O when the objective lens unit 110B is arranged on the optical axis O may be substantially the same as a position of the dichroic mirror DM1A on the optical axis O when the objective lens unit 110A is arranged on the optical axis O. Thereby, adjustment of the position and the orientation of the anterior segment photographing system 120 is not necessary when the photographing mode is switched.

The objective lens unit 110A may include the convex lenses 111A and 112A, and the concave lens 113A alone. And the objective lens unit 110B may include the convex lens 111B alone. Thereby, the dichroic mirrors DM1A and DM1B can be shared by one dichroic mirror when the objective lens unit arranged on the optical axis O is switched.

The objective lens system 110 is movable along the optical axis O by means of a movement mechanism (not illustrated, movement mechanism 110D described later). Thereby, the objective lens system 110 can be moved with respect to the optical system 100 in the Z direction. Therefore, both of a focus position of the SLO optical system 130 and a focus position of the OCT optical system 140 can be changed.

Hereinafter, a case where the objective lens unit 110A is arranged on the optical axis O will be mainly described.

(Anterior Segment Photographing System)

The anterior segment photographing system 120 includes an anterior segment illumination light source 121, a collimator lens 122, an anterior segment photographing camera 123, an imaging lens 124, and a beam splitter BS1. The beam splitter BS1 is an optical path coupling member to couple an optical path of the returning light of the illumination light for illuminating the anterior segment of the subject's eye E with an optical path of the illumination light.

The anterior segment illumination light source 121 is a light source for illuminating the anterior segment of the subject's eye E. The anterior segment photographing camera 123 includes an imaging element for detecting reflection light (returning light) from the anterior segment of the subject's eye E illuminated by the anterior segment illumination light source 121. As the anterior segment illumination light source 121, for example, an LED that emits light having a center wavelength of 950 nm is used. The light emitted from the anterior segment illumination light source 121 is collimated into a parallel light flux by the collimator lens 122. The illumination light having been collimated into the parallel light flux is reflected toward the dichroic mirror DM1A by the beam splitter BS1. The illumination light reflected by the beam splitter BS1 is deflected toward the subject's eye E by the dichroic mirror DM1A. The returning light of the illumination light from the subject's eye E is reflected by the dichroic mirror DM1A, and penetrates the beam splitter BS1. The returning light penetrating the beam splitter BS1 is condensed on a detection surface of the imaging element in the anterior segment photographing camera 123 by means of the imaging lens 124. The detection surface of the imaging element is arranged at the pupil conjugate position (anterior segment conjugate position) Q or near the position. The imaging element includes a charge-coupled device (CCD) or a complementary metal-oxide semiconductor (CMOS) image sensor, for example. The detection result of the returning light from the anterior segment of the subject's eye E obtained by the imaging element is used for forming an image of the anterior segment.

(SLO Optical System)

The dichroic mirror DM2 couples the optical path of the SLO optical system 130 with the optical path of the OCT optical system 140. At least a part of the SLO optical system 130 is formed as a telecentric optical system. Similarly, at least a part of the OCT optical system 140 is formed as a telecentric optical system. That is, the dichroic mirror DM2 couples an optical path formed by the telecentric optical system of the SLO optical system 130 with an optical path formed by the telecentric optical system of the OCT optical system 140. Thereby, an aberration of a pupil (e.g., an exit pupil by the objective lens system 110) becomes small even if the focus position of the optical system 100 is changed by moving the objective lens system 110. Therefore, a focus state can be adjusted easily.

For example, the dichroic mirrors DM1A (DM1B) and DM2 are arranged on the optical axis O with the twisted relationship maintained. The dichroic mirror DM1A (DM1B) has a first optical surface. One of at least part of light, which is guided through the optical path of the SLO optical system 130 and the optical path of the OCT optical system 140 (optical path of the optical system 100), and at least part of light, which is guided through the optical path of the anterior segment photographing system 120, is reflected by the first optical surface. Another of the at least part of light, which is guided through the optical path of the SLO optical system 130 and the optical path of the OCT optical system 140 (optical path of the optical system 100), and the at least part of light, which is guided through the optical path of the anterior segment photographing system 120, is transmitted through the first optical surface. The dichroic mirror DM2 has a second optical surface. One of at least part of light, which is guided through the optical path of the SLO optical system 130 and the optical path of the OCT optical system 140, is reflected by the second optical surface. Another of the at least part of light, which is guided through the optical path of the SLO optical system 130 and the optical path of the OCT optical system 140, is transmitted through the second optical surface. The dichroic mirrors DM1A (DM1B) and DM2 are arranged such that a plane including a normal line of the first optical surface and an optical axis of the SLO optical system 130 and a plane including a normal line of the second optical surface and the optical axis of the SLO optical system 130 are orthogonal to each other or substantially orthogonal to each other. In the high magnification photographing mode shown in FIG. 3, the concave lens 113A is not arranged between the dichroic mirror DM1B and the dichroic mirror DM2. Thereby, astigmatism can be removed or astigmatism can be made extremely small by the dichroic mirror DM1B and the dichroic mirror DM2, so that deterioration in image quality can be suppressed. On the other hand, in the wide-angle photographing mode shown in FIG. 1, the roughness of the image is allowed as compared with the high magnification photographing mode. Thereby, the influence on the image quality due to the remaining astigmatism can be reduced.

The SLO optical system 130 includes an SLO light source 131, a collimator lens 132, a beam splitter BS2, a condenser lens 133, a confocal diaphragm 134, a detector 135, an optical scanner 136, and a lens 137. The beam splitter BS2 is an optical path coupling member to couple an optical path of the return light of the SLO light projected onto the subject's eye E with an optical path of the SLO light.

The SLO light source 131 emits light having a center wavelength of 840 nm, for example. Examples of the SLO light source 131 include a laser diode (LD), a super-luminescent diode (SLD), a laser-driven light source (LDLS), and the like. The SLO light source 131 is arranged at a position (fundus conjugate position) P optically conjugate with the fundus (retina) or its vicinity.

Light emitted from the SLO light source 131 is collimated into a parallel light flux by a collimator lens 132. The light collimated into the parallel light flux is transmitted through the beam splitter BS2. The light transmitted through the beam splitter BS2 is deflected by the optical scanner 136. The optical scanner 136 is used to scan the fundus Ef of the subject's eye E with the light from the SLO light source 131. The optical scanner 136 includes an optical scanner 136X configured to deflect the light in the X direction and an optical scanner 136Y configured to deflect the light in the Y direction. The optical scanner 136X is a mirror whose tilt angle is variable. The tilt of the reflective surface of the mirror is controlled by a controller 200 described later. The optical scanner 136X is used for scanning in the horizontal direction of the fundus plane, for example. The optical scanner 136Y is located on the subject's eye E side with respect to the optical scanner 136X. The optical scanner 136Y is a mirror whose tilt angle is variable. The tilt of the reflective surface of the mirror is controlled by the controller 200. The optical scanner 136Y is used for scanning in the vertical direction, which is perpendicular to the horizontal direction, of the fundus plane, for example. Either one of the optical scanner 136X and the optical scanner 136Y may be a low-speed scanner such as a galvano mirror or the like, and the other may be a high-speed scanner such as a resonant mirror, a polygon mirror, a microelectromechanical systems (MEMS) mirror, or the like. The reflective surface of the optical scanner 136Y is arranged at a position (pupil conjugate position) Q optically conjugate with the pupil of the subject's eye E or near the position. The lens 137 and the dichroic mirror DM2 are located on the subject's eye E side with respect to the optical scanner 136Y. The light from the SLO light source 131 deflected by the optical scanner 136 is transmitted through the lens 137 and the dichroic mirror DM2, and is projected onto the subject's eye E via the objective lens system 110.

The returning light of the light from the SLO light source 131 projected onto the subject's eye E travels through the same optical path, and is reflected toward the detector 135 by the beam splitter BS2. The condenser lens 133 and the confocal diaphragm 134 are arranged between the beam splitter BS2 and the detector 135. The condenser lens 133 condenses the light reflected by the beam splitter BS2. The light condensed by the condenser lens 133 passes through an opening formed in the confocal diaphragm 134, and enters a detection surface of the detector 135. The opening formed in the confocal diaphragm 134 is arranged at a position (fundus conjugate position) P optically conjugate with the fundus (retina) or near the position. The detector 135 includes, for example, an avalanche photodiode (APD) or a photomultiplier tube (PMT).

(OCT Optical System)

OCT optical system 140 includes a focusing lens 141, an optical scanner 142, a collimator lens 143, and an interference optical system 150. The interference optical system 150 includes an OCT light source 151, a fiber coupler 152, a fiber coupler 153, a prism 154, and a detector 155.

The focusing lens 141 is movable along an optical axis (optical path) of the OCT optical system 140 by means of a movement mechanism (not illustrated, movement mechanism 141D described later). Thereby, a focus position of the OCT optical system 140 can be changed independently of the SLO optical system 130. Therefore, it is possible to finely adjust a focus state of the OCT optical system 140 by moving the focusing lens 141 after adjusting a focus state of the SLO optical system 130 and the OCT optical system 140 by moving the objective lens system 110, for example.

The optical scanner 142 is used to scan the fundus Ef of the subject's eye E with measurement light on the basis of light from the OCT light source 151. The optical scanner 142 includes an optical scanner 142X and an optical scanner 142Y. The optical scanner 142X deflects the light in the X direction. The optical scanner 142Y deflects the light in the Y direction. The optical scanner 142X is a mirror whose tilt angle is variable. The tilt of the reflective surface of the mirror is controlled by the controller 200. The optical scanner 142X is used for scanning in the horizontal direction of the fundus plane, for example. The optical scanner 142Y is located on the subject's eye E side of the optical scanner 142X. The optical scanner 142Y is a mirror whose tilt angle is variable. The tilt of the reflective surface of the mirror is controlled by the controller 200. The optical scanner 142Y is used for scanning in the vertical direction, which is perpendicular to the horizontal direction, of the fundus plane, for example. Either one of the optical scanner 142X and the optical scanner 142Y may be a low-speed scanner such as a low-speed galvano mirror or the like, and the other may be a high-speed scanner such as a high-speed galvano mirror or the like. An intermediate position between the optical scanners 142X and 142Y is arranged at a position (pupil conjugate position) Q optically conjugate with the pupil of the subject's eye E or near the position. The collimator lens 143 is located on the OCT light source 151 side with respect to the optical scanner 142Y. The controller 200 can control the optical scanner 142 independently of the optical scanner 136.

The interference optical system 150 includes an optical system for acquiring OCT images of the subject's eye E. The optical system has a similar configuration to a swept-source-type OCT apparatus known to the inventors. That is, the optical system is an interference optical system that splits light from the wavelength tunable type (wavelength scanning type) light source into measurement light and reference light, makes returning light of the measurement light from the subject's eye E and the reference light having traveled through a reference optical path interfere with each other to generate interference light, and detects the interference light. The interference optical system obtains a signal representing the spectrum of the interference light as the detection result (detection signal) of the interference light. It should be noted that the interference optical system 150 may have a configuration similar to that of a spectral-domain-type OCT apparatus known to the inventors, not a swept-source-type OCT apparatus.

The OCT light source 151 is a wavelength tunable type (i.e., a wavelength scanning type) light source capable of sweeping (scanning) the wavelengths of the OCT light (emitted light). A laser light source including a resonator and emitting light having a center wavelength of 1050 nm, for example, is used as the wavelength tunable type light source. The OCT light source 151 temporally changes the output wavelength in the near infrared wavelength band which cannot be visually recognized by the human eye.

Light L0 output from the OCT light source 151 is guided through an optical fiber f1 to the fiber coupler 152, and is divided into measurement light LS and reference light LR.

The reference light LR is guided to a fiber emitting end c1 through an optical fiber f2, and the collimator lens 156 is irradiated with the reference light LR emitted from the fiber emitting end c1. The reference light LR emitted from the fiber emitting end c1 is collimated into a parallel light flux by the collimator lens 156. The reference light LR, which has become a parallel light flux, is guided to the prism 154. The prism 154 changes the traveling direction of the reference light LR that has been made into the parallel light flux by the collimator lens 156 in the opposite direction. The optical path of the reference light LR incident on the prism 154 and the optical path of the reference light LR emitted from the prism 154 are parallel. The prism 154 is movable in a direction along the incident light path and the emitting light path of the reference light LR by means of a movement mechanism (not illustrated, a movement mechanism 154D described later). In this case, the movement mechanism is provided with an actuator that generates a driving force for moving the movement mechanism, and a transmission mechanism that transmits the driving force from the actuator to the movement mechanism. The actuator includes a pulse motor, for example. The transmission mechanism includes a combination of gears, a rack and pinion, and the like, for example. As a result, the length of the optical path of the reference light LR is changed.

The reference light LR that has traveled through the prism 154 is converted from the parallel light flux to the convergent light beam by a collimator lens 157 and enters a fiber entrance end c2 of an optical fiber f3, and is guided to the fiber coupler 153 through the optical fiber f3. It should be noted that an optical path length correction member or a dispersion compensation member is arranged between the collimator lens 156 or 157 and the prism 154. The optical path length correction member functions as a delaying means for matching the optical path length (i.e., optical distance) of the reference light LR with the optical path length of the measurement light LS. The dispersion compensation member functions as a dispersion compensation means for matching the dispersion characteristics between the reference light LR and the measurement light LS.

On the other hand, the measurement light LS generated by the fiber coupler 152 is guided to a fiber end c3 through an optical fiber f4. The collimator lens 143 is irradiated with the measurement light LS guided to the fiber end c3. The measurement light LS emitted from the fiber end c3 is collimated into a parallel light flux by the collimator lens 143. The measurement light LS collimated into a parallel light flux reaches the dichroic mirror DM2 via the optical scanner 142 and the focusing lens 141. The measurement light LS is reflected by the dichroic mirror DM2, and is refracted by the objective lens system 110. The subject's eye E is irradiated with the measurement light LS. The measurement light LS is scattered (and reflected) at various depth positions of the subject's eye E. The returning light of the measurement light LS including such backscattered light advances through the same path as the outward path in the opposite direction and is led to the fiber coupler 152, and then reaches the fiber coupler 153 through an optical fiber f5.

The fiber coupler 153 generates the interference light by superposing the measurement light LS incident through the optical fiber f5 and the reference light LR incident through the optical fiber f3 with each other (i.e., by making the measurement light LS incident through the optical fiber f5 and the reference light LR incident through the optical fiber f3 interfere with each other). The fiber coupler 153 generates a pair of interference light LC by splitting the interference light generated from the measurement light LS and the reference light LR at a predetermined splitting ratio (for example, 1:1). The pair of interference light LC output from the fiber coupler 153 is guided to the detector 155.

The detector 155 is, for example, a balanced photodiode that includes a pair of photodetectors for respectively detecting the pair of interference light LC and outputs the difference between the pair of detection results obtained by the pair of photodetectors. The detector 155 sends the detection result (detection signal) to an unillustrated data acquisition system (DAQ). The DAQ is fed with a clock from the OCT light source 151. The clock is generated in the OCT light source 151 in synchronization with the output timing of each wavelength sweeping (i.e., wavelength scanning) within a predetermined wavelength range performed by the wavelength tunable type light source. The DAQ performs the sampling of the detection result obtained by the detector 155 based on the clock, and send it to an image forming unit described later and the like. The image forming unit applies Fourier transform and the like to the spectral distribution based on the detection result obtained by the detector 155, for example, with respect to a series of wavelength scans (for each A-line) to form the reflection intensity profile in each A-line. In addition, the image forming unit forms image data by applying imaging processing to the reflection intensity profiles of the respective A lines.

[Processing System]

Figure 4A:
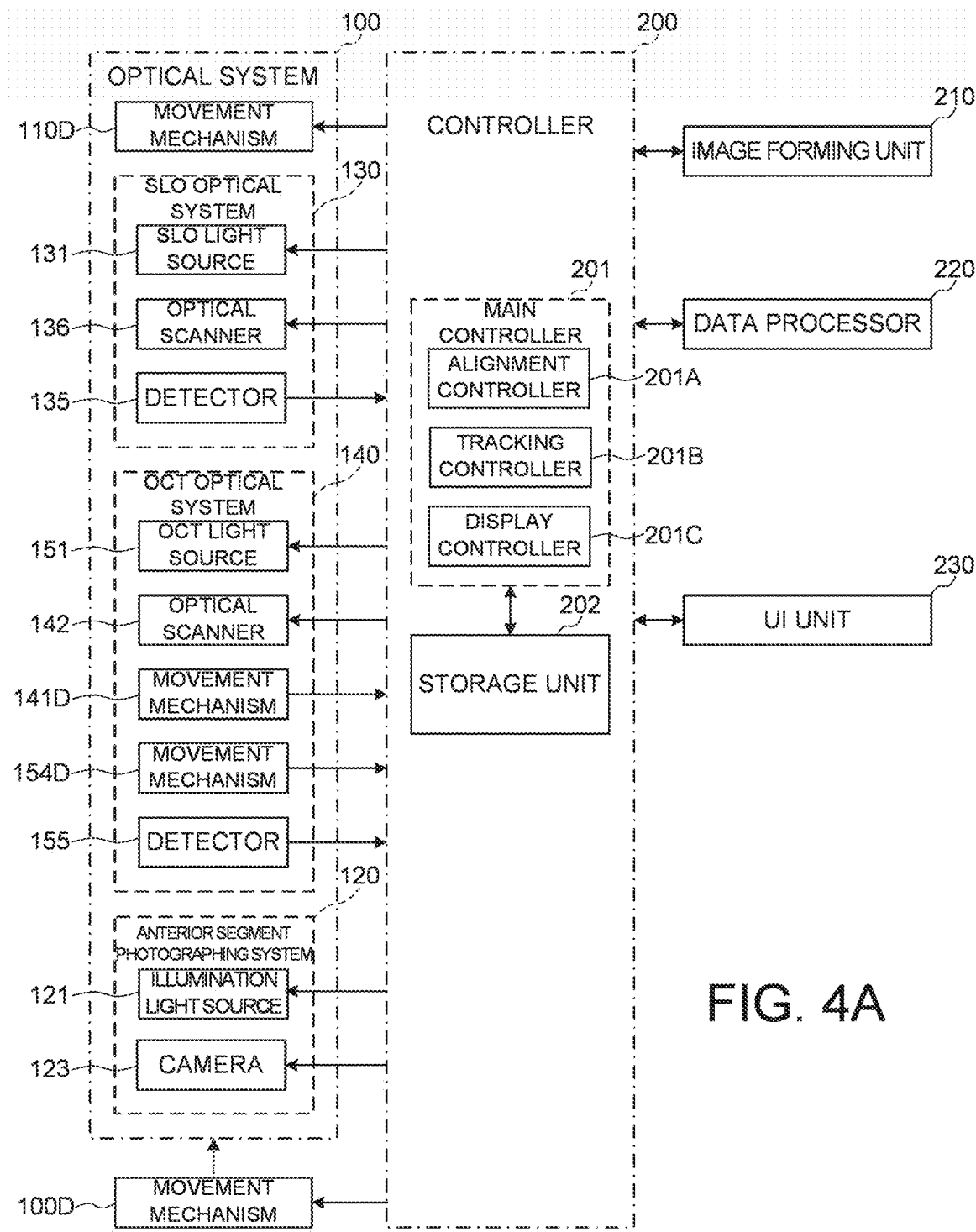
FIG. 4A is a schematic diagram illustrating an example of the configuration of a processing system of the ophthalmologic apparatus according to the embodiments.

FIGS. 4A to 4E illustrate examples of the configuration of the optical system of the ophthalmologic apparatus according to the embodiments. In FIG. 4A, like reference numerals designate like parts as in FIGS. 1 and 3. The same description may not be repeated. In FIGS. 4B to 4E, like reference numerals designate like parts in FIG. 4A, and the redundant explanation may be omitted as appropriate.

(Controller)

As shown in FIG. 4A, the controller 200 is the center of the processing system of the ophthalmologic apparatus according to the embodiments. The controller 200 controls each part of the ophthalmologic apparatus. The controller 200 includes a main controller 201 and a storage unit 202. The functions of the main controller 201 is realized by a processor, for example. The storage unit 202 stores, in advance, a computer program for controlling the ophthalmologic apparatus. The computer program includes, for example, various light source control programs, optical scanner control program, various detector control programs, image forming program, data processing program, program for user interface, and the like. The main controller 201 (processor) operates according to the computer programs, and thereby the controller 200 performs the control process.

The function of the "processor" is implemented by a circuit(s) such as, for example, a CPU (central processing unit), a GPU (graphics processing unit), an ASIC (application specific integrated circuit), and a PLD (programmable logic device). Examples of PLD include a simple programmable logic device (SPLD), a complex programmable logic device (CPLD), and a field programmable gate array (FPGA).

Examples of the control of the objective lens system 110 include control of the movement mechanism 110D that moves the objective lens system 110 along the optical axis O, and the like. For example, the movement mechanism 110D is provided with an actuator that generates a driving force for moving the movement mechanism 110D and a transmission mechanism that transmits the driving force from the actuator to the movement mechanism 110D. The actuator includes a pulse motor, for example. The transmission mechanism includes a combination of gears, a rack and pinion, and the like, for example. The main controller 201 controls the movement mechanism 110D by sending a control signal to the actuator.

Examples of the control of the SLO optical system 130 include control of the SLO light source 131, control of the optical scanner 136, control of the detector 135, and the like. Examples of the control of the SLO light source 131 includes turning on and off the light source, adjustment of amount of light, adjustment of aperture, and the like. Examples of the control of the optical scanner 136 include control of the scan position and the scan range by means of the optical scanner 136X, control of the scan position and the scan range by means of the optical scanner 136Y, and the like. Examples of the control of the detector 135 include adjustment of exposure of a detecting element, adjustment of gain of a detecting element, adjustment of detecting rate of a detecting element, and the like.

Examples of the control of the OCT optical system 140 include control of the OCT light source 151, control of the optical scanner 142, control of the movement mechanism 141D and the movement mechanism 154D, control of the detector 155, and the like. Examples of the control of the OCT light source 151 includes turning on and off of the light source, adjustment of amount of light, adjustment of aperture, and the like. Examples of the control of the optical scanner 142 include control of the scan position and the scan range by means of the optical scanner 142X, control of the scan position and the scan range by means of the optical scanner 142Y, and the like. The movement mechanism 141D moves the focusing lens 141 along the optical path of the OCT optical system 140. For example, the movement mechanism 141D is provided with an actuator that generates a driving force for moving the movement mechanism 141D and a transmission mechanism that transmits the driving force from the actuator to the movement mechanism 141D. The actuator includes a pulse motor, for example. The transmission mechanism includes a combination of gears, a rack and pinion, and the like, for example. The main controller 201 controls the movement mechanism 141D by sending a control signal to the actuator. The movement mechanism 154D moves the prism 154 in a direction along the incident light path and the emitting light path of the reference light LR. For example, the movement mechanism 154D is provided with an actuator that generates a driving force for moving the movement mechanism 154D and a transmission mechanism that transmits the driving force from the actuator to the movement mechanism 154D. The actuator includes a pulse motor, for example. The transmission mechanism includes a combination of gears, a rack and pinion, and the like, for example. The main controller 201 controls the movement mechanism 154D by sending a control signal to the actuator. Examples of the control of the detector 155 include adjustment of exposure of a detecting element, adjustment of gain of a detecting element, adjustment of detecting rate of a detecting element, and the like.

Examples of the control of the anterior segment photographing system 120 include control of the anterior segment illumination light source 121, control of the anterior segment photographing camera 123, and the like. Examples of control of the anterior segment illumination light source 121 include turning on and off the light source, adjustment of an amount of light, adjustment of aperture, and the like. The control of the anterior segment photographing camera 123 include adjustment of exposure of the imaging devices, adjustment of gain of the imaging devices, adjustment of photographing rate of the imaging devices, and the like.

Examples of the control of the optical system 100 (including the dichroic mirrors DM1A and DM1B, and the anterior segment photographing system 120) include control of the movement mechanism 100D that moves the optical system 100 in the X direction, the Y direction, and the Z direction, and the like. For example, the movement mechanism 100D is provided with an actuator that generates a driving force for moving the movement mechanism 100D and a transmission mechanism that transmits the driving force from the actuator to the movement mechanism 100D. The actuator includes a pulse motor, for example. The transmission mechanism includes a combination of gears, a rack and pinion, and the like, for example. The main controller 201 controls the movement mechanism 100D by sending a control signal to the actuator.

The main controller 201 includes an alignment controller 201A, a tracking controller 201B, and a display controller 201C.

The alignment controller 201A controls the perform of the alignment for position matching of the optical system 100 with respect to the subject's eye E. The alignment controller 201A controls the movement mechanisms 100D and 110D based on the anterior segment image of the subject's eye E acquired by the anterior segment photographing system 120. For example, the alignment controller 201A specifies a characteristic site of the anterior segment images of the subject's eye E acquired by the anterior segment photographing system 120, and obtains a movement amount of the optical system 100 and the like so as to cancel a displacement amount between the specified characteristic site and a predetermined target position. The alignment controller 201A controls the movement mechanism 100D based on the obtained movement amount to perform position matching of the optical system 100 with respect to the subject's eye E (in the X direction and in the Y direction). The target position may be a predetermined position, or the target position may be a position in the anterior segment image designated using a UI unit 230.

For example, the alignment controller 201A can specify an in-focus state (degree of blur) of the anterior segment image of the subject's eye E acquired by the anterior segment photographing system 120, and can obtain a movement amount of the objective lens system 110 in the Z direction so that the specified in-focus state becomes a desired in-focus state. The alignment controller 201A controls the movement mechanisms 100D and 110D based on the obtained movement amount to perform position matching of the optical system 100 and the objective lens system 110 with respect to the subject's eye E (in the Z direction). It should be noted that the anterior segment may be photographed from different directions using two or more camera, the in-focus state may be specified three-dimensionally from two or more images with parallax, and the movement amount of the objective lens system 110 in the Z direction may be obtained so that the specified in-focus state becomes a desired in-focus state.

The alignment controller 201A may control the movement mechanism 110D based on an SLO image acquired by the SLO optical system 130 to perform position matching of the objective lens system 110 with respect to the subject's eye E (in the Z direction). In this case, the alignment controller 201A specifies an in-focus state (degree of blur) of the acquired SLO image, and obtains a movement amount of the objective lens system 110 in the Z direction so that the specified in-focus state becomes a desired in-focus state. The alignment controller 201A controls the movement mechanism 110D based on the obtained movement amount.

The tracking controller 201B performs control of tracking based on the SLO image of the subject's eye E acquired by the SLO optical system 130. The tracking controller 201B is capable of obtaining a displacement (misregistration) amount (including a displacement direction) of the target image with reference to the base image, and of performing control of tracking based on the obtained displacement amount. The base image is the SLO image of the fundus Ef of the subject's eye E obtained in advance. The target image is the SLO image of the fundus Ef obtained after acquiring the base image. Here, the target image is an image acquired by scanning a scan region narrower than a scan region in acquiring the base image. The tracking controller 201B can perform control of tracking based on the displacement amount between a partial image and the target image. The partial image is an image corresponding to the target image in the base image. The displacement amount of the target image with respect to the partial image is obtained by performing phase-only correlation processing. The tracking controller 201B can control the movement mechanism 100D and/or the optical scanner 136 based on the obtained displacement amount.

Further, the tracking controller 201B can control the optical scanner 142 based on the obtained displacement amount. For example, the tracking controller 201B corrects a scan position of the optical scanner 142 based on the obtained displacement amount.

The display controller 201C causes the user interface unit 230 described later to display various kinds of information. Examples of the information displayed on the user interface unit 230 include information generated by the controller 200, image formed by the image forming unit 210, information after data processing performed by the data processor 220, and the like.

(Image Forming Unit)

The image forming unit (image former) 210 forms various types of images (image data). The various images (the various image data) formed by the image forming unit 210 are stored in the storage unit 202, for example.

Figure 4B:
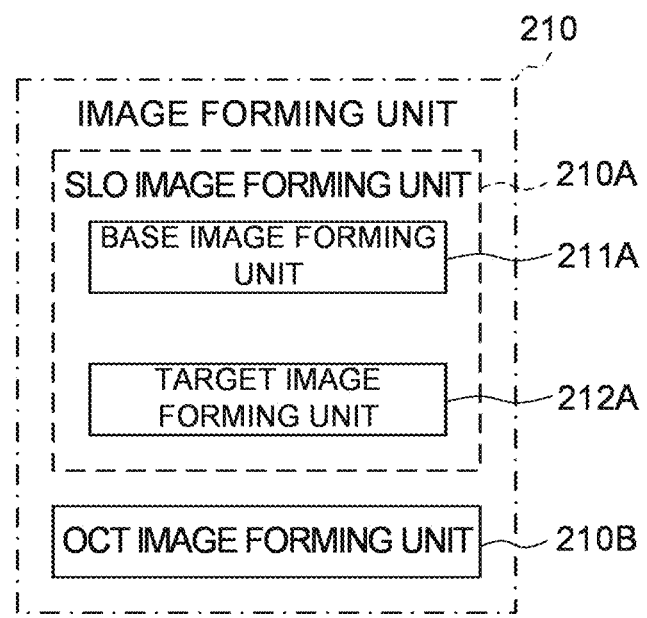
FIG. 4B is a schematic diagram illustrating an example of the configuration of a processing system of the ophthalmologic apparatus according to the embodiments.

As shown in FIG. 4B the image forming unit 210 includes an SLO image forming unit (image former) 210A and an OCT image forming unit (image former) 210B. In some embodiments, the functions of the image forming unit 210 are realized by one or more processors. In some embodiments, the function of each part of the image forming unit 210 is realized by one or more processors.

The SLO image forming unit 210A forms image data of the SLO image based on the detection signal input from the detector 135 and a pixel position signal input from the controller 200. The SLO image forming unit 210A includes a base image forming unit (image former) 211A and a target image forming unit (image former) 212A. The base image forming unit 211A forms the base image based on a scan result of a scan region corresponding to the base image. The target image forming unit 212A forms the target image based on a scan result of a scan region corresponding to the target image.

The OCT image forming unit 210B forms image data of the OCT image (tomographic image of the fundus Ef) based on the detection signal input from the detector 155 and a pixel position signal input from the controller 200.

Further, the image forming unit 210 can form an anterior segment image based on the detection result of the reflection light from the anterior segment of the subject's eye E obtained by the imaging element(s) in the anterior segment photographing camera 123.

(Data Processor)

The data processor 220 performs various types of data processing. Examples of the data processing include processing on the image data formed by the image forming unit 210 or another apparatus. Examples of the processing include various types of image processing, analyzing processing on images, and diagnosis support processing such as image evaluation based on the image data, and the like.

The data processor 220 obtains a displacement amount between the partial image and the target image. Here, the partial image is an image corresponding to the target image in the base image acquired in advance. And then, the data processor 220 outputs information corresponding to the obtained displacement amount to the controller 200 (the main controller 201). The displacement amount includes a rotational movement amount, a rotational movement direction thereof, a parallel movement amount, and a parallel movement direction thereof, and the like. The rotational movement amount is an amount at sub-pixel level (less than 1 pixel) in a rotation direction (rotation direction around the axis in the Z direction) between the partial image and the target image. The parallel movement amount is an amount at sub-pixel level in the XY plane between the partial image and the target image.

Specifically, the data processor 220 calculates the rotational movement amount and the rotational movement direction between the partial image and the target image at the sub-pixel level, and performs position matching (registration) between the partial image and the target image in the rotation direction based on the calculated rotational movement amount and the calculated rotational movement direction. And then, the data processor 220 calculates the parallel movement amount and the parallel movement direction between the partial image and the target image at the sub-pixel level. Here, the partial image and the target image have been already performed position matching.

Figure 4C:
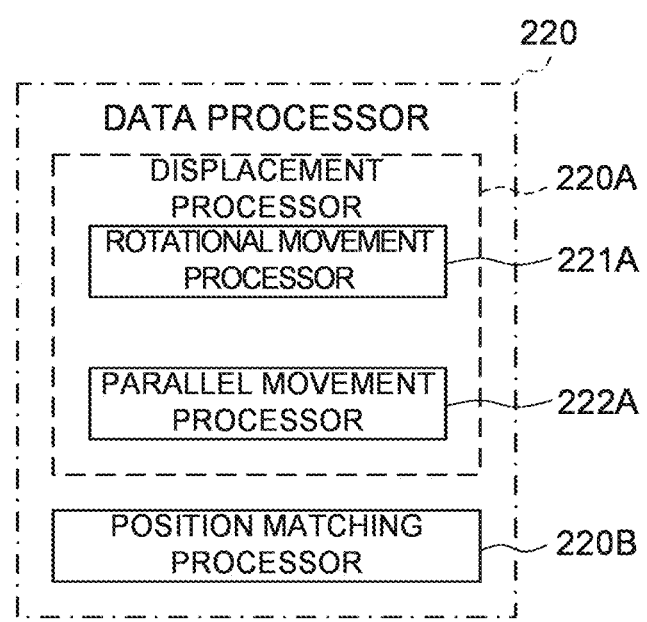
FIG. 4C is a schematic diagram illustrating an example of the configuration of a processing system of the ophthalmologic apparatus according to the embodiments.

As shown in FIG. 4C, such the specifying unit 220 includes a displacement processor 220A and a position matching processor 220B. The displacement processor 220A obtains a displacement (including displacement amount and displacement direction) of the target image with respect to the partial image based on the partial image in the base image and the target image as described above. The position matching processor 220B performs position matching (i.e., registration) between the partial image and the target image. In some embodiments, the functions of the data processor 220 are realized by one or more processors. In some embodiments, the function of each part of the data processor 220 is realized by one or more processors.

The displacement processor 220A includes a rotational movement processor 221A and a parallel movement processor 222A.

The rotational movement processor 221A calculates a rotational movement amount and a rotational movement direction between the partial image and the target image. The rotational movement processor 221A can calculate the rotational movement amount and the rotational movement direction between the partial image and the target image by performing phase-only correlation processing on the partial image and the target image. Such the phase-only correlation processing is similar to the processing disclosed in Japanese Unexamined Patent Application Publication No. 2015-043898.

In the phase-only correlation processing according to the embodiments, for example, the following phase-only correlation function is used. Hereinafter, a partial image corresponding to the target image in the base image may be referred to as a "base image".

First, it is assumed that the partial image (base image) having an image size of $N_1 \times N_2$ ($N_1$ and $N_2$ are positive integers) is represented by $f(n_1, n_2)$, and the target image having an image size of $N_1 \times N_2$ is represented by $g(n_1, n_2)$. It is also assumed herein that, in the discrete space, $n_1 = -M_1, \ldots, M_1$, $N_1 = 2M_1+1$ ($M_1$ is a positive integer), and the result of two-dimensional discrete Fourier transform (DFT) on $f(n_1, n_2)$ is $F(k_1, k_2)$. Then, $F(k_1, k_2)$ is represented by Equation (1) as follows:

[Equation 1]

$$F(k_1, k_2) = \sum_{n_1=-M_1}^{M_1} \sum_{n_2=-M_2}^{M_2} f(n_1, n_2) W_{N_1}^{k_1 n_1} W_{N_2}^{k_2 n_2} = A_F(k_1, k_2) e^{j\theta_F(k_1, k_2)} \quad (1)$$

$$\left( k_1 = -M_1, \ldots, M_1, M_2, k_2 = -M_2, \ldots, M_2, W_{N_1} = e^{-j\frac{2\pi}{N_1}}, W_{N_2} = e^{-j\frac{2\pi}{N_2}} \right)$$

In Equation (1), $A_F(k_1, k_2)$ is the amplitude component of $f(n_1, n_2)$, and $e^{j\theta_F(k_1, k_2)}$ is the phase component of $f(n_1, n_2)$.

Similarly, it is assumed that, in the discrete space, $n_2 = -M_2, \ldots, M_2$, $N_2 = 2M_2+1$ ($M_2$ is a positive integer), and the result of two-dimensional DFT of $g(n_1, n_2)$ is $G(k_1, k_2)$. Then, $G(k_1, k_2)$ is represented by Equation (2) as follows:

[Equation 2]

$$G(k_1, k_2) = \sum_{n_1=-M_1}^{M_1} \sum_{n_2=-M_2}^{M_2} g(n_1, n_2) W_{N_1}^{k_1 n_1} W_{N_2}^{k_2 n_2} = A_G(k_1, k_2) e^{j\theta_G(k_1, k_2)} \quad (2)$$

$$\left( k_1 = -M_1, \ldots, M_1, M_2, k_2 = -M_2, \ldots, W_{N_1} = e^{-j\frac{2\pi}{N_1}}, W_{N_2} = e^{-j\frac{2\pi}{N_2}} \right)$$

In Equation (2), $A_G(k_1, k_2)$ is the amplitude component of $g(n_1, n_2)$, and $e^{j\theta_G(k_1, k_2)}$ is the phase component of $g(n_1, n_2)$.

Using Equations (1) and (2), the phase-only synthesis function used in the phase-only synthesis processing is defined by Equation (3) as follows:

[Equation 3]

$$\hat{R}(k_1, k_2) = \frac{F(k_1, k_2)\overline{G(k_1, k_2)}}{|F(k_1, k_2)\overline{G(k_1, k_2)}|} = e^{j\theta(k_1, k_2)} \quad (3)$$

($\overline{G(k_1, k_2)}$ is the complex conjugate of $G(k_1, k_2)$, $\theta(k_1, k_2) = \theta_F(k_1, k_2) - \theta_G(k_1, k_2)$)

By applying a two-dimensional inverse discrete Fourier transform (IDFT) to the phase-only synthesis function represented by Equation (3), the phase-only correlation function according to the embodiments is represented by Equation (4) as follows:

[Equation 4]

$$\hat{r}(n_1, n_2) = \frac{1}{N_1 N_2} \sum_{k_1=-M_1}^{M_1} \sum_{k_2=-M_2}^{M_2} \hat{R}(k_1, k_2) W_{N_1}^{-k_1 n_1} W_{N_2}^{-k_2 n_2} \quad (4)$$

An image obtained by shifting a two-dimensional image $s_c(x_1, x_2)$ defined in a continuous space by a minute movement amount $\delta_1$ in the $x_1$ direction and by a minute movement amount $\delta_2$ in the $x_2$ direction is represented as $s_c(x_1-\delta_1, x_2-\delta_2)$. The two-dimensional image $f(n_1, n_2)$ sampled at a sampling interval $T_1$ in the discrete space is defined by Equation (5) as follows:

[Equation 5]

$$f(n_1, n_2) = s_c(x_1, x_2)|_{x_1=n_1 T_1, x_2=n_2 T_2} \quad (5)$$

Similarly, the two-dimensional image $g(n_1, n_2)$ sampled at a sampling interval $T_2$ in the discrete space is defined by Equation (6) as follows:

[Equation 6]

$$g(n_1, n_2) = s_c(x_1-\delta_1, x_2-\delta_2)|_{x_1=n_1 T_1, x_2=n_2 T_2} \quad (6)$$

In Equations (5) and (6), and $n_1 = -M_1, \ldots, M_1$, $n_2 = -M_2, \ldots, M_2$. Thus, the phase-only correlation function related to the two-dimensional images $f(n_1, n_2)$ and $g(n_1, n_2)$ in the discrete space is represented in general form as Equation (7) as follows: In Equation (7), $\alpha=1$.

[Equation 7]

$$\hat{r}(n_1, n_2) \approx \frac{\alpha}{N_1 N_2} \frac{\sin\{\pi(n_1+\delta_1)\}}{\sin\left\{\frac{\pi}{N_1}(n_1+\delta_1)\right\}} \frac{\sin\{\pi(n_2+\delta_2)\}}{\sin\left\{\frac{\pi}{N_2}(n_2+\delta_2)\right\}} \quad (7)$$

Figure 4D:
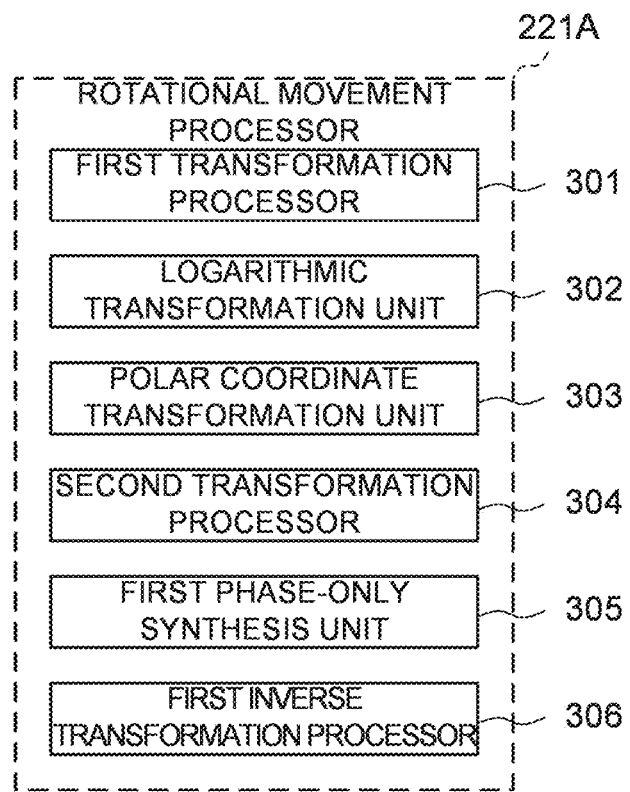
FIG. 4D is a schematic diagram illustrating an example of the configuration of a processing system of the ophthalmologic apparatus according to the embodiments.
Figure 4E:
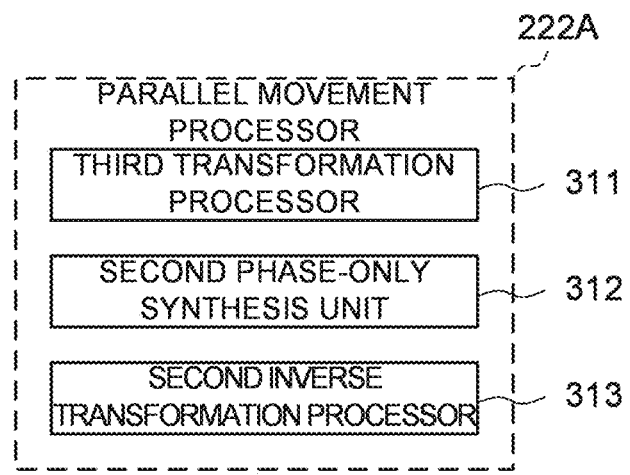
FIG. 4E is a schematic diagram illustrating an example of the configuration of a processing system of the ophthalmologic apparatus according to the embodiments.

As shown in FIG. 4D, the rotational movement processor 221A includes a first transformation processor 301, a logarithmic transformation unit 302, a polar coordinate transformation unit 303, a second transformation processor 304, a first phase-only synthesis unit 305, and a first inverse transformation processor 306.

The first transformation processor 301 performs two-dimensional DFT processing on the partial image (base image). Further, the first transformation processor 301 performs two-dimensional DFT processing on the target image. The two-dimensional DFT processing performed by the first transformation processor 301 includes two-dimensional DFT, and a known shift processing for shifting the quadrant with respect to the result of the two-dimensional DFT. Hereinafter, this shift processing may be referred to as "shift". Note that the two-dimensional DFT performed by the first transformation processor 301 may be two-dimensional FFT.

The logarithmic transformation unit 302 applies a logarithmic transformation to the calculation result obtained by the first transformation processor 301 for the partial image (base image). Further, the logarithmic transformation unit 302 applies a logarithmic transformation also to the calculation result obtained by the first transformation processor 301 for the target image. The logarithmic transformation performed by the logarithmic transformation unit 302 has the effect of compressing the amplitude spectrum that has a tendency to concentrate in the low-frequency region of the spatial frequency in a natural image.

The polar coordinate transformation unit 303 applies a polar coordinate transformation to the calculation result obtained by the logarithmic transformation unit 302 for the partial image (base image). Further, the polar coordinate transformation unit 303 applies a polar coordinate transformation also to the calculation result obtained by the logarithmic transformation unit 302 for the target image. When the logarithmic transformation is not performed by the logarithmic transformation unit 302, the polar coordinate transformation unit 303 applies a polar coordinate transformation to the calculation result obtained by the first transformation processor 301 for the partial image (base image), and applies a polar coordinate transformation to the calculation result obtained by the first transformation processor 301 for the target image. The polar coordinate transformation performed by the polar coordinate transformation unit 303 is the processing of converting the movement amount in the rotation direction into the movement amount in the parallel direction (in the $n_1$ direction and in the $n_2$ direction) in Equations (1) to (7).

As illustrated in Equation (1), the second transformation processor 304 performs the two-dimensional DFT processing (two-dimensional DFT+shift) on the calculation result obtained by the polar coordinate transformation unit 303 for the partial image (base image). Prior to the arithmetic processing of the first phase-only synthesis unit 305, the processing result obtained by the second transformation processor 304 for the partial images (base image) is stored in, for example, the storage unit 202 in advance as the base POC data normalized by the amplitude component. As illustrated in Equation (2), the second transformation processor 304 performs the two-dimensional DFT processing (two-dimensional DFT+shift) on the calculation result obtained by the polar coordinate transformation unit 303 for the target image. Incidentally, the two-dimensional DFT performed by the second transformation processor 304 may also be two-dimensional FFT.

As illustrated in Equation (3), the first phase-only synthesis unit 305 performs a phase-only synthesis processing for synthesizing the base POC data (first data) previously obtained for the partial image (base image) and target POC data (second data). The target POC data is data normalized by the amplitude component based on the calculation result obtained by the second transformation processor 304 for the target image.

The first inverse transformation processor 306 performs a two-dimensional IDFT processing on the calculation result obtained by the first phase-only synthesis unit 305. The two-dimensional IDFT processing performed by the first inverse transformation processor 306 includes two-dimensional IDFT, and a known shift processing for shifting the quadrant with respect to the result of the two-dimensional IDFT. Note that the two-dimensional IDFT may be a two-dimensional inverse fast Fourier transform (IFFT).

The rotational movement processor 221A calculates a rotational movement amount and a rotational movement direction based on the calculation result obtained by the first inverse transformation processor 306. Specifically, the rotational movement processor 221A specifies a peak position based on the calculation result obtained by the first inverse transformation processor 306 to thereby calculate the rotational movement amount and the rotational movement direction at the pixel level. The rotational movement processor 221A then specifies a pixel position at which the correlation value of the phase-only correlation function represented by Equation (7) becomes the maximum in the vicinity of the peak position specified at the pixel level, thereby obtaining the rotational movement amount and the rotational movement direction at the sub-pixel level.

The rotational movement processor 221A need not necessarily calculate the rotational movement amount and the rotational movement direction using the phase-only correlation processing. The rotational movement processor 221A may calculate the rotational movement amount and the rotational movement direction by a known technique.

The parallel movement processor 222A calculates a parallel movement amount and a parallel movement direction between the partial image (base image) and the target image which have been performed position matching by the position matching processor 220B described later. The parallel movement processor 222A applies phase-only correlation processing to the partial image and the target image. Here, the partial image and the target image have been already performed position matching by the position matching processor 220B. And the parallel movement processor 222A obtains the parallel movement amount and the parallel movement direction between the partial image and the target image. Such the phase-only correlation processing is similar to the processing disclosed in Japanese Unexamined Patent Application Publication No. 2015-043898.

The parallel movement processor 222A calculates the parallel movement amount and the parallel movement direction between the partial image and the target image which have been performed position matching by position matching processor 220B. Specifically, the parallel movement processor 222A applies phase-only correlation processing to the partial image and the target image which have been performed position matching by the position matching processor 220B to obtain the parallel movement amount and the parallel movement direction between the partial image and the target image.

The parallel movement processor 222A includes a third transformation processor 311, a second phase-only synthesis unit 312, and a second inverse transformation processor 313.

As illustrated in Equation (1), the third transformation processor 311 performs the two-dimensional DFT processing (two-dimensional DFT+shift) on the partial image (base image). Prior to the arithmetic processing of the second phase-only synthesis unit 312, the processing result obtained by the third transformation processor 311 for the partial image is stored in, for example, the storage unit 202 in advance as the base POC data (third data) normalized by amplitude component. As illustrated in Equation (2), the third transformation processor 311 performs the two-dimensional DFT processing (two-dimensional DFT+shift) on the target image. Incidentally, the two-dimensional DFT performed by the third transformation processor 311 may also be two-dimensional FFT.

As illustrated in Equation (3), the second phase-only synthesis unit 312 performs a phase-only synthesis processing for synthesizing the base POC data (third data) previously obtained for the partial image (base image) and target POC data (fourth data). The target POC data is a data normalized by amplitude component based on the calculation result obtained by the third transformation processor 311 for the target image.

The second inverse transformation processor 313 performs a two-dimensional IDFT processing (two-dimensional IDFT+shift) on the calculation result obtained by the second phase-only synthesis unit 312. The two-dimensional IDFT performed by the second inverse transformation processor 313 may be two-dimensional IFFT.

The parallel movement processor 222A calculates a parallel movement amount and a parallel movement direction based on the calculation result obtained by the second inverse transformation processor 313. Specifically, the parallel movement processor 222A specifies a peak position based on the calculation result obtained by the second inverse transformation processor 313 to thereby obtain the parallel movement amount and the parallel movement direction at the pixel level. The parallel movement processor 222A then specifies the pixel position at which the correlation value of the phase-only correlation function represented by Equation (7) becomes the maximum in the vicinity of the peak position specified at the pixel level, thereby obtaining the parallel movement amount and the parallel movement direction at the sub-pixel level.

The position matching processor 220B performs position matching (registration) in the rotation direction between the partial image and the target image based on the rotational movement amount and the rotational movement direction obtained by the rotational movement processor 221A. Specifically, the position matching processor 220B performs position matching on the target image with reference to the partial image in the rotation direction based on the rotational movement amount and the rotational movement direction calculated by the rotational movement processor 221A. Incidentally, the position matching processor 220B may perform position matching on the partial image with reference to the target image in the rotation direction based on the rotational movement amount and the rotational movement direction calculated by the rotational movement processor 221A.

(User Interface Unit)

The user interface unit 230 has a function for interchanging information between a user and the ophthalmologic apparatus. The user interface unit 230 includes a display device and an operation device (input device). The display devices may include a display unit, and it may include another display device. The operation device includes various hardware keys and/or software keys. Upon receiving the operation content for the operation device, the controller 200 can output a control signal corresponding to the operation content to each part of the ophthalmologic apparatus. At least a part of the display device and at least a part of the operation device may be configured integrally. One example of this is the touch panel display.

The light (SLO light) emitted from the SLO light source 131 and transmitted through the beam splitter BS2 is an example of the "first light" according to the embodiments. The optical scanner 136 is an example of the "first optical scanner" according to the embodiments. The subject's eye E is an example of the "target eye" according to the embodiments. The SLO optical system 130 is an example of the "SLO system" according to the embodiments. The measurement light LS is an example of the "second light" according to the embodiments. The optical scanner 142 is an example of the "second optical scanner" according to the embodiments. The OCT optical system 140 is an example of the "projection system" or the "OCT system" according to the embodiments. The base image is an example of the "first image" according to the embodiments. The base image forming unit 211A is an example of the "first image former (forming unit)" according to the embodiments. The target image is an example of the "second image" according to the embodiments. The target image forming unit 212A is an example of the "second image former (forming unit)" according to the embodiments. The OCT image forming unit 210B is an example of the "third image former (forming unit)" according to the embodiments.

Operation Example

Operation examples of the ophthalmologic apparatus according to the embodiments will be described.

Figure 5:
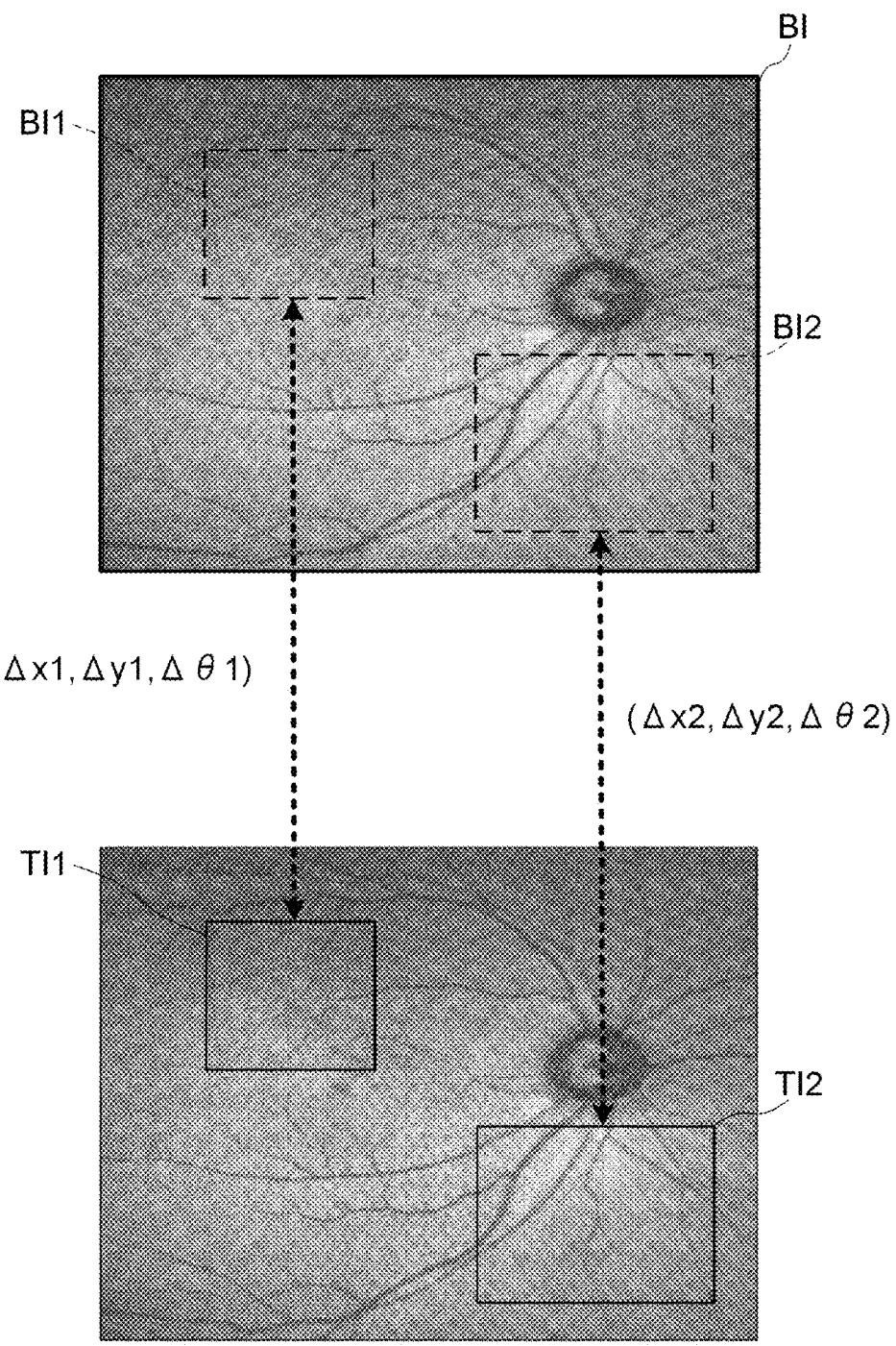
FIG. 5 is an explanatory diagram of the operation of the ophthalmologic apparatus according to the embodiments.

FIG. 5 shows a diagram describing an example of the operation of the ophthalmologic apparatus according to the embodiments. FIG. 5 illustrates a diagram describing of a partial image in the base image and the target image according to the embodiments.

In the embodiments, when the base image (SLO image) BI of the fundus Ef of the subject's eye E is acquired, the target images (TI1, TI2, . . . ) of the fundus Ef are sequentially acquired by scanning a scan region narrower than a scan region when the base image was acquired. Each time each of the target images (TI1, TI2, . . . ) is acquired, the displacement amount between the acquired target image and the partial image (BI1, BI2, . . . ) corresponding to the acquired target image in the base image is obtained.

For the partial image BI1 and the target image TI1, the rotational movement processor 221A calculates $\Delta\theta1$ representing the rotational movement amount and the rotational direction of the target image TI1 with respect to the partial image BI1. Further, the parallel movement processor 222A calculates $\Delta x1$ and $\Delta y1$ representing the parallel movement amount and the parallel movement direction of the target image TI1 with respect to the partial image BI1.

In the same way, for the partial image BI2 and the target image TI2, the rotational movement processor 221A calculates $\Delta\theta2$ representing the rotational movement amount and the rotational direction of the target image TI2 with respect to the partial image BI2. Further, the parallel movement processor 222A calculates $\Delta x2$ and $\Delta y2$ representing the parallel movement amount and the parallel movement direction of the target image TI2 with respect to the partial image BI2.

The tracking controller 201B corrects a scan position of the optical scanner 142 based on the displacement amount ($\Delta x1$, $\Delta y1$, $\Delta\theta1$) of the target image TI1 with respect to the partial image BI1. Subsequently, when the target image TI2 is acquired, the tracking controller 201B corrects a scan position of the optical scanner 142 based on the displacement amount ($\Delta x2$, $\Delta y2$, $\Delta\theta2$) of the target image TI2 with respect to the partial image BI2.

That is, the main controller 201 (tracking controller 201B) is configured to control the SLO optical system 130 (optical scanner 136) so as to scan repeatedly while changing the position of the scan region in subject's eye E for acquiring the target image. And, each time scanning of the scan region is completed, the main controller 201 is configured to cause the target image forming unit 212A to form the target image, to cause the displacement processor 220A to calculate the displacement amount (displacement), and to control the optical scanner 142 based on the calculated displacement amount. The main controller 201 (tracking controller 201B) can repeatedly perform scan of the scan region of the optical scanner 136 so as to scan the entire scan region when the base image is acquired.

Figure 6:
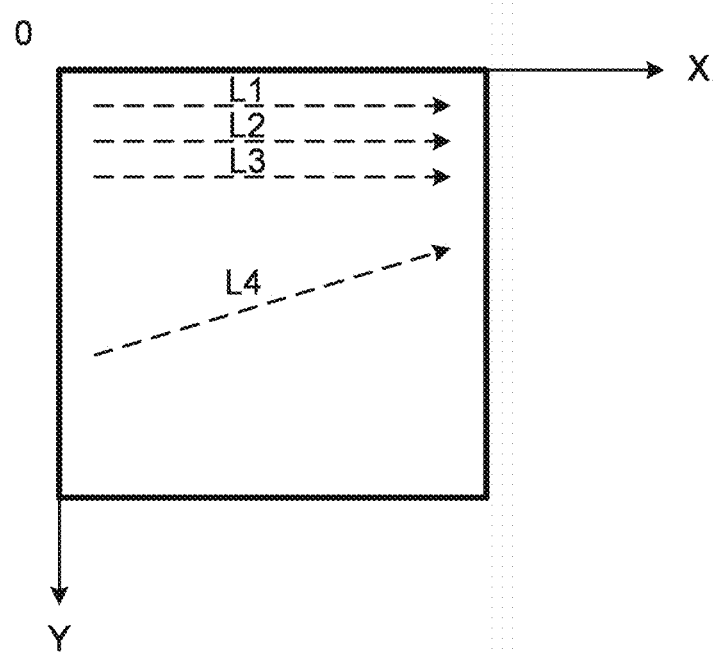
FIG. 6 is an explanatory diagram of the operation of the ophthalmologic apparatus according to the embodiments.

FIG. 6 schematically shows an example of scan position correction according to the embodiments. FIG. 6 schematically represents the scan region in case that a line scan along the X direction is sequentially moved in the Y direction by the optical scanner 142 in the OCT optical system 140.

For example, when the displacement amount ($\Delta x$, $\Delta y$, $\Delta\theta$) is obtained by the displacement processor 220A described above after the line scans L1 to L3 are performed, the tracking controller 201B rotates the direction of the line scan L4 whose scan end position is (xe, ye) by "$-\Delta\theta$". Then, the tracking controller 201B corrects the scan position so that the scan end position of the line scan L4 is (xe+h1($\Delta x$), ye+h2($\Delta y$)). Here, h1 and h2 are predetermined functions. For example, when k is an arbitrary coefficient, the tracking controller 201B can correct the scan position by ($-k\times\Delta x$) in the X direction and ($-k\times\Delta y$) in the Y direction.

Figure 7:
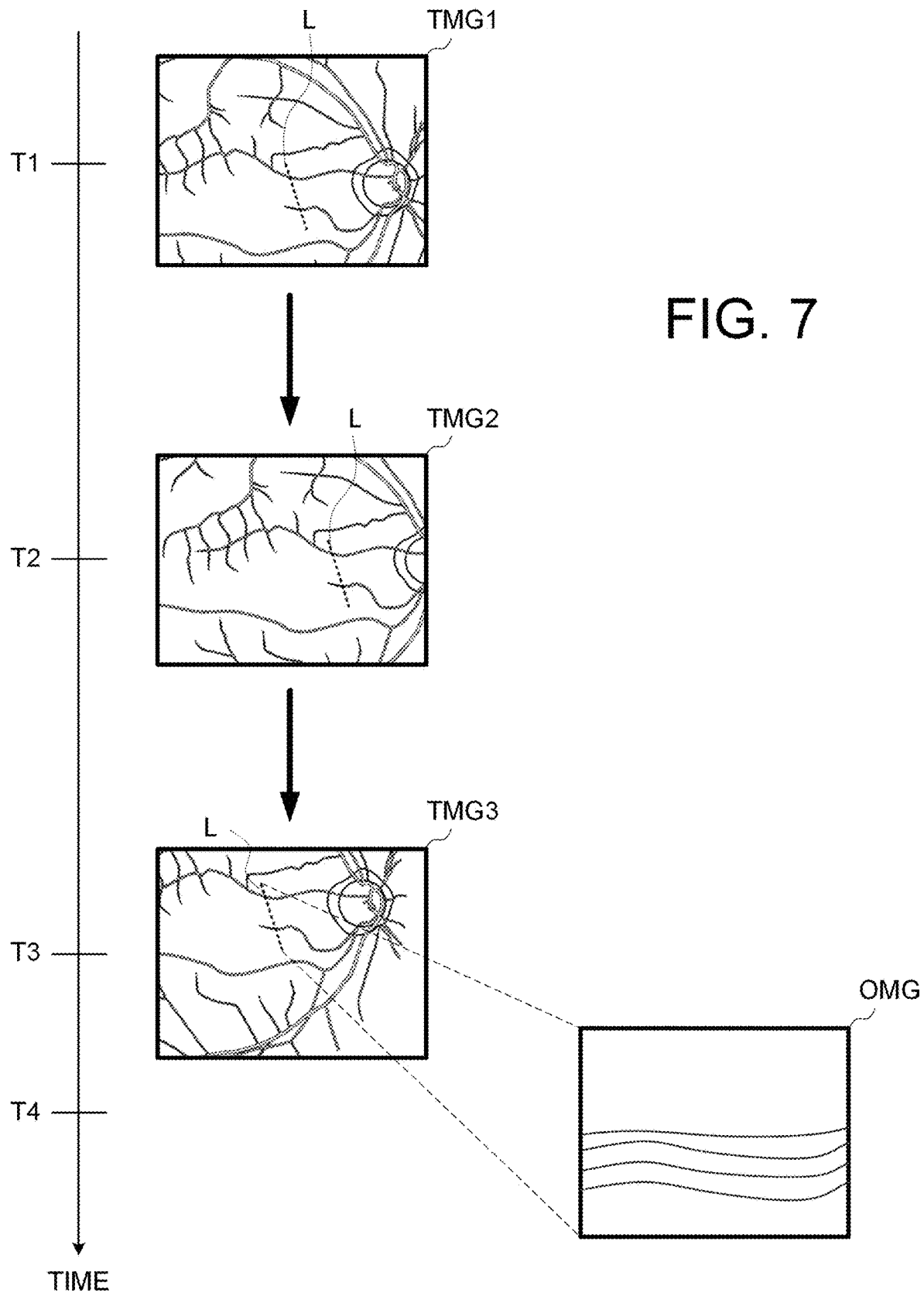
FIG. 7 is an explanatory diagram of the operation of the ophthalmologic apparatus according to the embodiments.

FIG. 7 is an explanatory diagram of tracking control in the ophthalmologic apparatus according to the embodiments. FIG. 7 schematically represents the target image and the OCT image at times T1, T2, and T3 during scanning of the scan line L. It should be noted that the position of the scan line L performed by the OCT optical system 140 is schematically illustrated in each target image. FIG. 7 schematically illustrates the case where the target image is translated relative to the base image, but the same applies to the case where the target image is rotated relative to the base image.

It is assumed that the target image TMG1 is acquired at time T1, and scanning of the scan line L is started by the OCT optical system 140.

When the target image acquired at time T2 moves with respect to the base image due to eye movement between times T1 and T2, the displacement processor 220A obtains the displacement amount and the tracking controller 201B corrects the scan position of the optical scanner 142 based on the obtained displacement amount, described above. Thereby, at time T2, scanning is continued at the position of the scan line L in the target image TMG2.

In the same way, when the target image acquired at time T3 moves with respect to the base image due to eye movement between times T2 and T3, the displacement processor 220A obtains the displacement amount and the tracking controller 201B corrects the scan position of the optical scanner 142 based on the obtained displacement amount, described above. Thereby, at time T3, scanning is continued at the position of the scan line L in the target image TMG2.

In this way, the scan position of the optical scanner 142 follows the eyeball movement between times T1 and T3. At time T4 after time T3, an OCT image OMG is formed based on the scan result on the scan line L (FIG. 7).

As described above, according to the embodiments, the scan position of the optical scanner 142 is corrected using the target image obtained by scanning the scan region narrower than the base image. Thereby, the target image can be acquired in a short time even when the SLO optical system 130 is used. Therefore, it can also follow eye movement during acquisition of an SLO image and perform high-speed tracking control.

Further, the displacement amount of the target image with respect to the partial image of the base image is obtained using phase-only correlation processing. Thereby, tracking control can be performed with high precision. In addition, by performing scan for acquiring the next target image while calculating the displacement amount, tracking control can be performed at higher speed.

In the above embodiments, the position of the scan region for acquiring the target image is changed so as to change the position of the partial image in the base image. However, the position of the scan region on the fundus Ef may be determined so that the position of the partial image in the base image becomes a fixed position. In this case, the processing for specifying the position of the partial image in the base image can be simplified.

Further, the position of the scan region on the fundus Ef for acquiring the target image may be changed so that the base image is covered by a plurality of partial images. In this case, tracking control can be performed based on the morphology (form) of the fundus Ef drawn in a wide range in the base image. Thereby, the accuracy of tracking can be improved.

In addition, when the target image is acquired by scanning the scan region of the same size as the base image, it is conceivable to perform distortion correction on the acquired target image in consideration of distortion in order to reduce the error of the displacement amount. On the other hand, according to the embodiments, the scan region for acquiring the target image can be narrowed. Thereby, distortion correction processing and the like can be eliminated.

Further, when the size of each scan region (the size of the target image) is known in calculating the displacement amount, the sizes of the scan regions for acquiring the target image may not be the same. For example, the data processor 220 may include an analyzer for specifying a characteristic site of the fundus Ef. The size of the scan region including the region corresponding to the characteristic site specified by the analyzer may be wider than other scan regions. Thereby, the accuracy of tracking can be improved.

Further, the size of the scan region for acquiring the target image may be changed at the next scan. For example, when the displacement amount between the target image and the partial image equals to or greater than a predetermined threshold value, the size of the scan region may be enlarged when the next target image is acquired.

Further, in the fundus Ef, at least a part of the scan region for acquiring the target image may be overlap with the scan region for acquiring another target image.

In the following description, it is assumed that the position of the scan region for acquiring the target image is sequentially moved in the X direction so that the partial image corresponding to the target image becomes an image obtained by dividing the base image BI in the X direction. Here, the X direction is the scanning direction of the optical scanner 136 (optical scanner 142).

Figure 8:
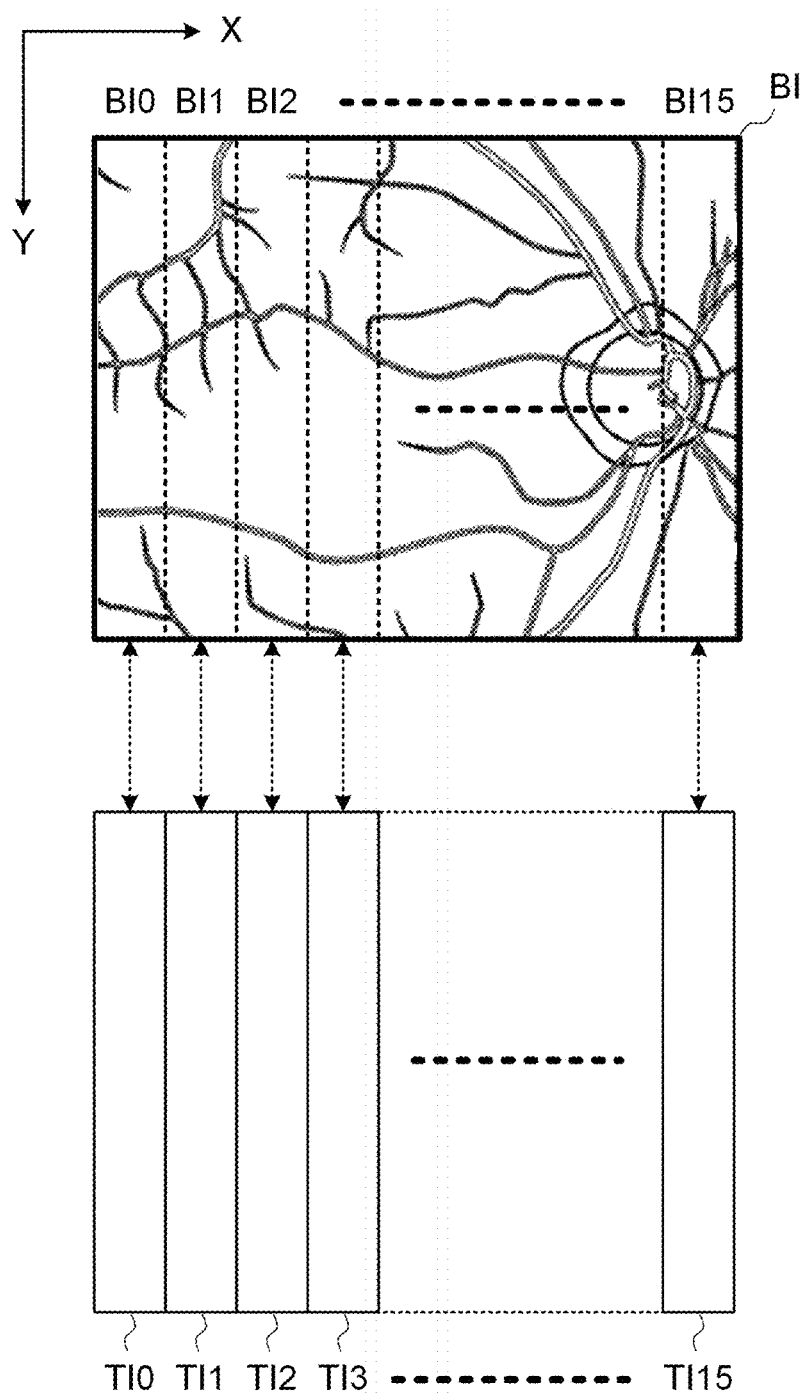
FIG. 8 is an explanatory diagram of the operation of the ophthalmologic apparatus according to the embodiments.

FIG. 8 shows a diagram describing the partial image according to the embodiments. FIG. 8 represents the partial images BI0 to BI15 obtained by dividing the base image BI into 16 equal intervals in the X direction. That is, the partial images BI0 to BI15 have the same size in the Y direction and the same size in the X direction.

The main controller 201 controls the SLO optical system 130 so as to sequentially scan the scan regions set to acquire the target image shown in FIG. 8. The main controller 201 causes the target image forming unit 212A to sequentially form the target images TI0 to TI15. Each of the target images TI0 to TI15 is an image in which the size in the Y direction is the same as the size in the Y direction of the base image BI, and the size in the X direction is 1/16 of the size in the X direction of the base image BI. Each time the target image is acquired, the main controller 201 causes the displacement processor 220A to calculate the displacement amount between the target image and the partial image corresponding to the target image, and controls the optical scanner 142 based on the calculated displacement amount.

Figure 9:
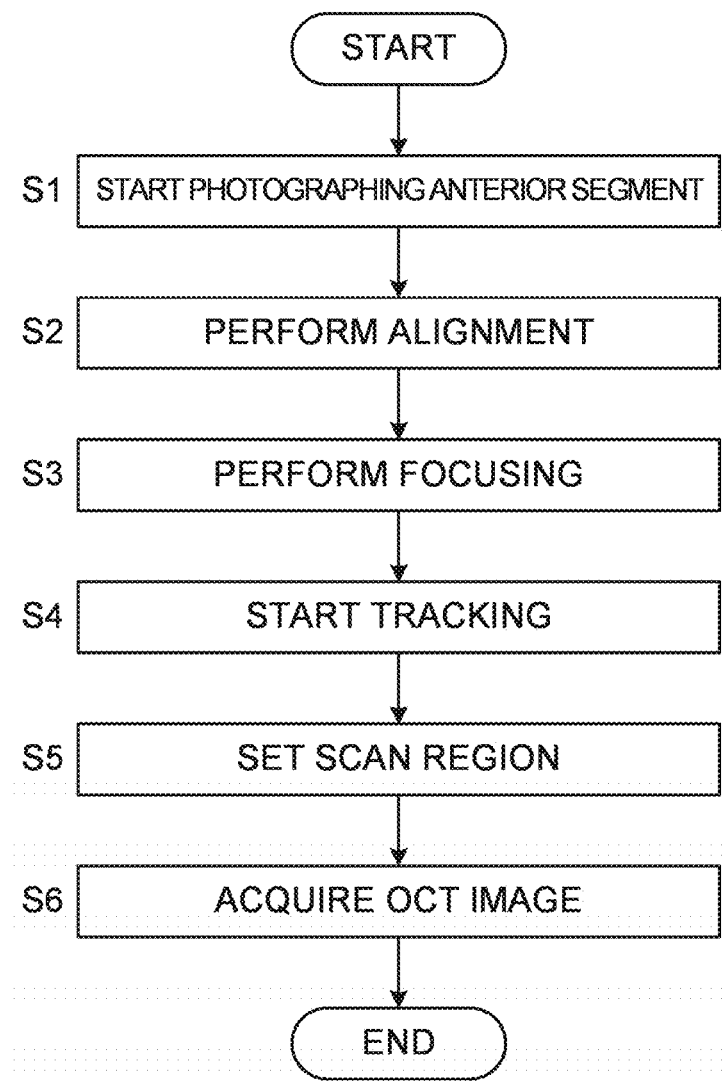
FIG. 9 is a flow chart of an operation example of the ophthalmologic apparatus according to the embodiments.

FIG. 9 shows a flow chart of an operation example of the ophthalmologic apparatus according to the embodiments. In FIG. 9, for example, it is assumed that the objective lens unit 110A for the wide-angle photographing mode is set on the optical axis O.

(S1: Start Photographing Anterior Segment)

First, the main controller 201 causes the anterior segment illumination light source 121 to continuously illuminate the fundus Ef with illumination light from the anterior segment illumination light source 121. Then, the main controller 201 starts acquiring an anterior segment image using the anterior segment photographing camera 123.

(S2: Perform Alignment)

The alignment controller 201A controls the movement mechanism 100D based on the anterior segment image acquired in step S1, thereby performing position matching of the optical system 100 and the objective lens system 110 with respect to the subject's eye E (in the X direction and the Y direction). For example, the alignment controller 201A controls the movement mechanism 100D so that the position of the characteristic site (the position of the region corresponding to the pupil) in the anterior segment image specified by the data processor 220 is a predetermined position.

(S3: Perform Focusing)

The main controller 201 moves the scan positions of the optical scanners 136 and 142 to predetermined initial positions. The main controller 201 turns on the SLO light source 131 and controls the optical scanner 136 to start scanning the fundus Ef of the subject's eye E with the light from the SLO light source 131. The SLO image forming unit 210A forms the SLO image of the fundus Ef based on the detection result of the fundus reflection light obtained by the detector 135.

The alignment controller 201A performs alignment in the focus direction (in the Z direction) of the retina from the anterior segment image obtained in step S1 or the SLO image obtained in step S3. Thereby, the position of the objective lens system 110 can be finely adjusted in the optical axis O direction.

(S4: Start Tracking)

The tracking controller 201B starts control of tracking. The tracking controller 201B can perform tracking control for the SLO image and tracking control for the OCT image.

(S5: Set Scan Region)

The main controller 201 causes the display unit of the UI unit 230 to display the SLO image in real time. The user sets a scan region on SLO image using the operation unit of the UI unit 230. The scan region may be a one-dimensional region or a two-dimensional region.

(S6: Acquire OCT Image)

The main controller 201 controls the OCT optical system 140. The main controller 201 controls the optical scanner 142 based on the scan region set in step S5 to perform OCT measurement of the fundus Ef. The OCT image forming unit 210B forms a tomographic image of the fundus Ef based on a detection signal obtained. In case that three-dimensional scan is set as the scan mode, the data processor 220 forms a three-dimensional image of the fundus Ef based on a plurality of tomographic images formed by the OCT image forming unit 210B. With this, the operation example ends (END).

Figure 10:
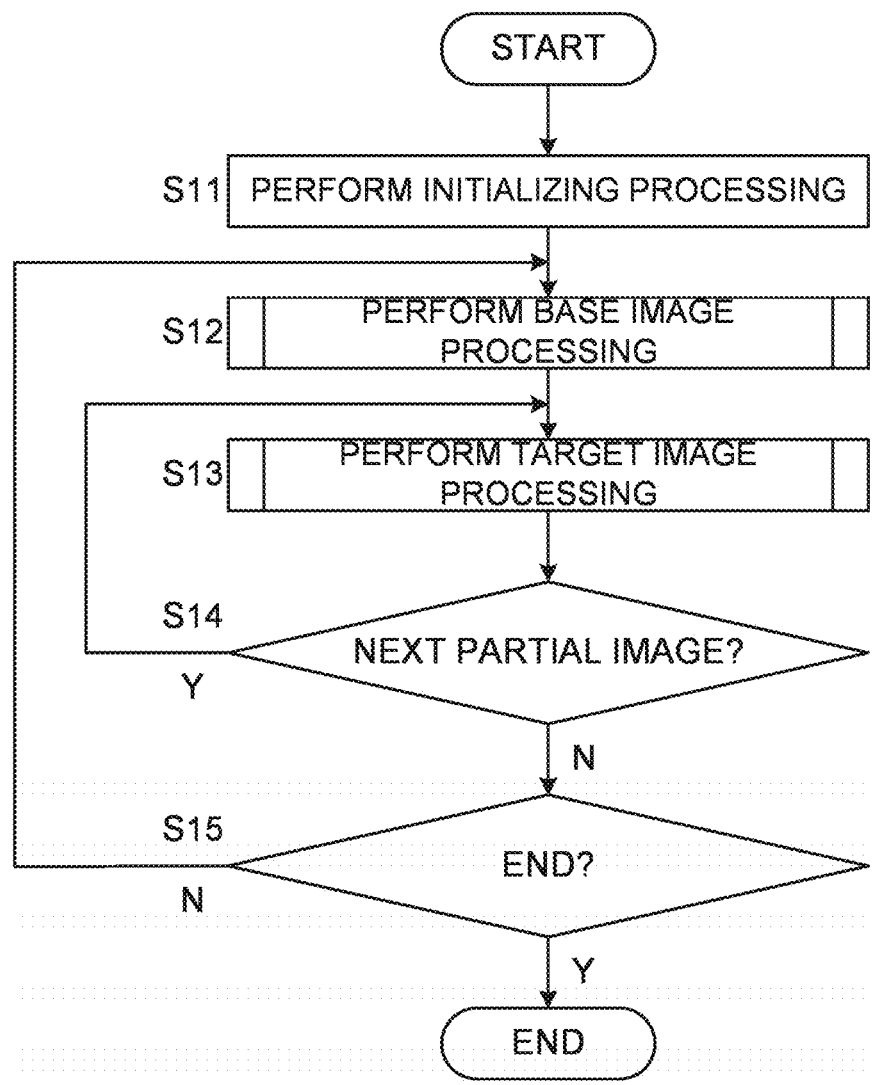
FIG. 10 is a flow chart of an operation example of the ophthalmologic apparatus according to the embodiments.

FIG. 10 shows a flow chart of a processing example of the tracking control according to the embodiments. For example, when the subject's eye is changed or the photographing mode is changed, the processing shown in FIG. 10 is performed.

(S11: Perform Initializing Processing)

First, the main controller 201 performs predetermined initializing processing. Examples of the initializing processing include securing resources, setting the scan regions for acquiring the base image and the target image, initializing the displacement processor 220A, and the like.

(S12: Perform Base Image Processing)

Next, the main controller 201 causes the displacement processor 220A to perform base image processing for performing phase-only correlation processing on the partial image corresponding to the target image. The partial image is an image corresponding to the target image in the base image. The base image processing is described in detail later.

(S13: Perform Target Image Processing)

Subsequently, the main controller 201 causes the displacement processor 220A to perform target image processing for performing phase-only correlation processing on the target images input sequentially. In the target image processing, processing for tracking control on the basis of the partial image and the target image is performed. Here, the partial image corresponds to the target image. The target image processing is described in detail later.

(S14: Next Partial Image?)

The main controller 201 determines whether or not the next partial image should be processed. In the embodiments, the base image is divided into 16 partial image areas as shown in FIG. 8, and target image processing is sequentially performed on each partial image area.

When it is determined that the next partial image should be processed (S14: Y), the operation of the ophthalmologic apparatus proceeds to step S13. When it is determined that the next partial image should not be processed (S14: N), the operation of the ophthalmologic apparatus proceeds to step S15.

(S15: END?)

When it is determined in the step S14 that the next partial image should not be processed (S14: N), the main controller 201 determines whether or not to end photographing. When it is determined that the photographing is not to be ended (S15: N), the operation of the ophthalmologic apparatus proceeds to S12. That is, when the target image processing is performed on the target images (TI0 to TI15) corresponding to all the partial images (BI0 to BI15), the target image processing is sequentially performed from the target image (TI0) corresponding to the first partial image (BI0) again. When it is determined that the photographing is to be ended (S15: Y), the ophthalmologic apparatus terminates the processing for tracking control (END).

Next, the base image processing in step S12 will be described.

Figure 11:
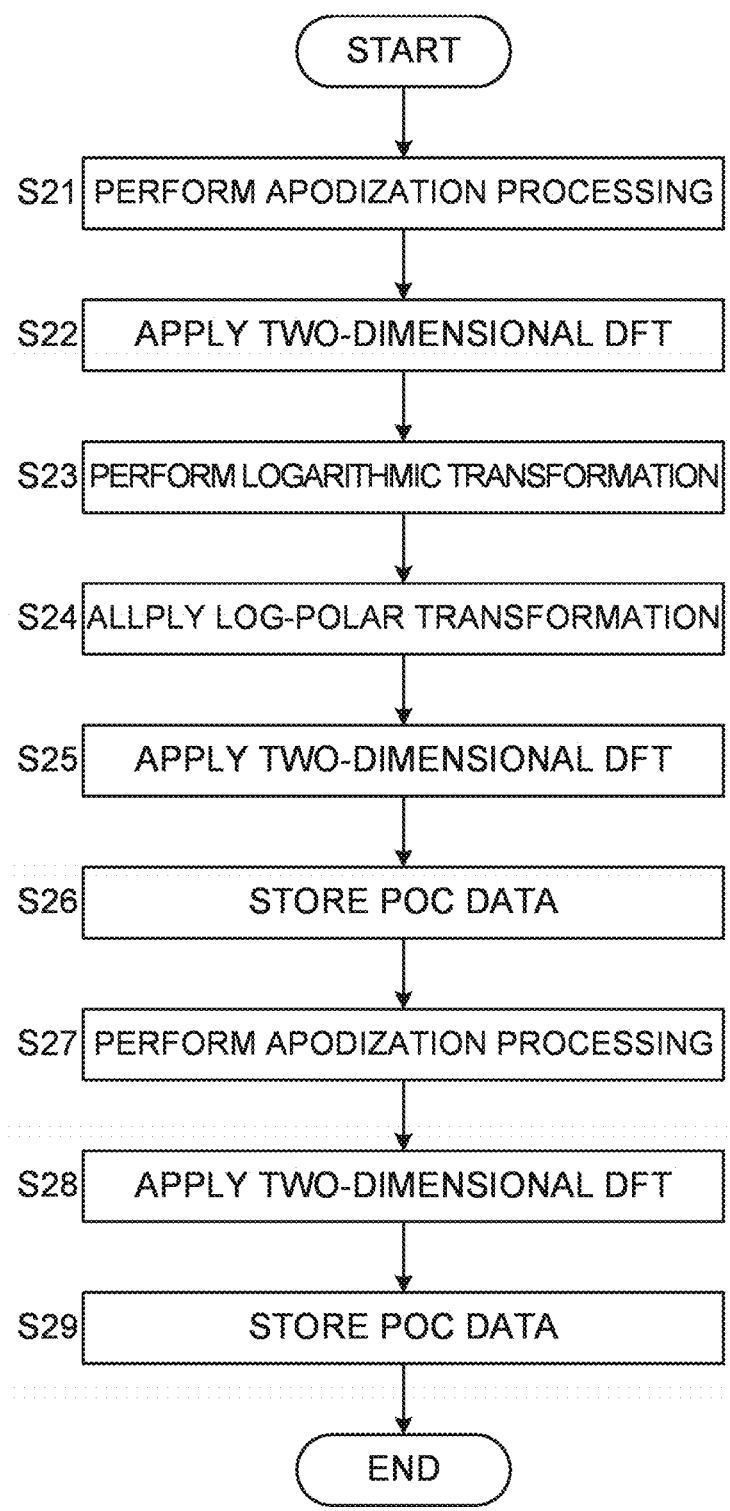
FIG. 11 is a flow chart of an operation example of the ophthalmologic apparatus according to the embodiments.

FIG. 11 shows an example of a flow of the base image processing according to the embodiments. The base image processing shown in FIG. 11 is performed for each partial image of the base image.

(S21: Perform Apodization Processing)

First, the rotational movement processor 221A performs apodization processing on the partial image (base image) corresponding to the target image. The apodization processing is processing to increase the dynamic range through multiplication by an apodization function to reduce the amplitude of side lobes as well as suppressing to some extent a decrease in the amplitude of the main lobe. Examples of the apodization function include window functions such as a known Hanning window, Gaussian window, rectangular window, and the like. The apodization processing is performed by, for example, an apodization processor (not illustrated) in the first transformation processor 301 or the rotational movement processor 221A.

(S22: Apply Two-Dimensional DFT)

Next, the first transformation processor 301 applies a two-dimensional DFT to the result of the apodization processing performed on the partial image in step S21.

(S23: Perform Logarithmic Transformation)

Next, the logarithmic transformation unit 302 applies a logarithmic transformation to the processing result of the two-dimensional DFT in step S22. The logarithmic transformation is represented by Equation (8) as follows: where Re is the real component of the result of the two-dimensional DFT, Im is the imaginary component thereof, and Am is the result of the logarithmic transformation. This compresses the amplitude spectrum that tends to be concentrated in the low-frequency region of spatial frequencies in a natural image.

[Equation 8]

$$Am = 20 \times \log_{10}(\sqrt{Re^2 + Im^2} + 1) \tag{8}$$

(S24: Apply Log-Polar Transformation)

Next, the polar coordinate transformation unit 303 applies a Log-Polar transformation to the processing result of the logarithmic transformation in step S23. Thus, the radius direction is changed to the X direction, and the argument direction is changed to the Y direction.

(S25: Apply Two-Dimensional DFT)

Next, the second transformation processor 304 applies a two-dimensional DFT to the processing result of the Log-Polar transformation in step S24.

(S26: Store POC Data)

Next, the rotational movement processor 221A performs normalization with the amplitude component based on the processing result of the two-dimensional DFT in step S25, and stores it in the storage unit 202 as first base POC data on the basis of the processing result of the two-dimensional DFT. Here, the first base POC data stored in the storage unit 202 is used to calculate a correlation value of the phase-only correlation function for calculating the rotational movement amount and the rotational direction.

(S27: Perform Apodization Processing)

Subsequently, the parallel movement processor 222A generates base POC data used to calculate a correlation value of the phase-only correlation function for calculating the parallel movement amount and the parallel movement direction for the partial image. Therefore, the parallel movement processor 222A performs the apodization processing on the partial image. The apodization processing is performed in the same manner as described in step S21. In case that the processing result of step S21 is stored in the storage unit 202, the process of step S27 can be made unnecessary.

(S28: Apply Two-Dimensional DFT)

Next, the third transformation processor 311 applies a two-dimensional DFT to the real component of the result of the apodization processing performed on the partial image.

(S29: Store POC Data)

Next, the parallel movement processor 222A performs normalization with the amplitude component based on the processing result of the two-dimensional DFT in step S28, and stores it in the storage unit 202 as second base POC data on the basis of the processing result of the two-dimensional DFT. Here, the second base POC data stored in the storage unit 202 is used to calculate a correlation value of the phase-only correlation function for calculating the parallel movement amount and the parallel movement direction. With this, a series of processes of the base image processing is completed (END).

Next, the target image processing in step S13 will be described.

Figure 12:
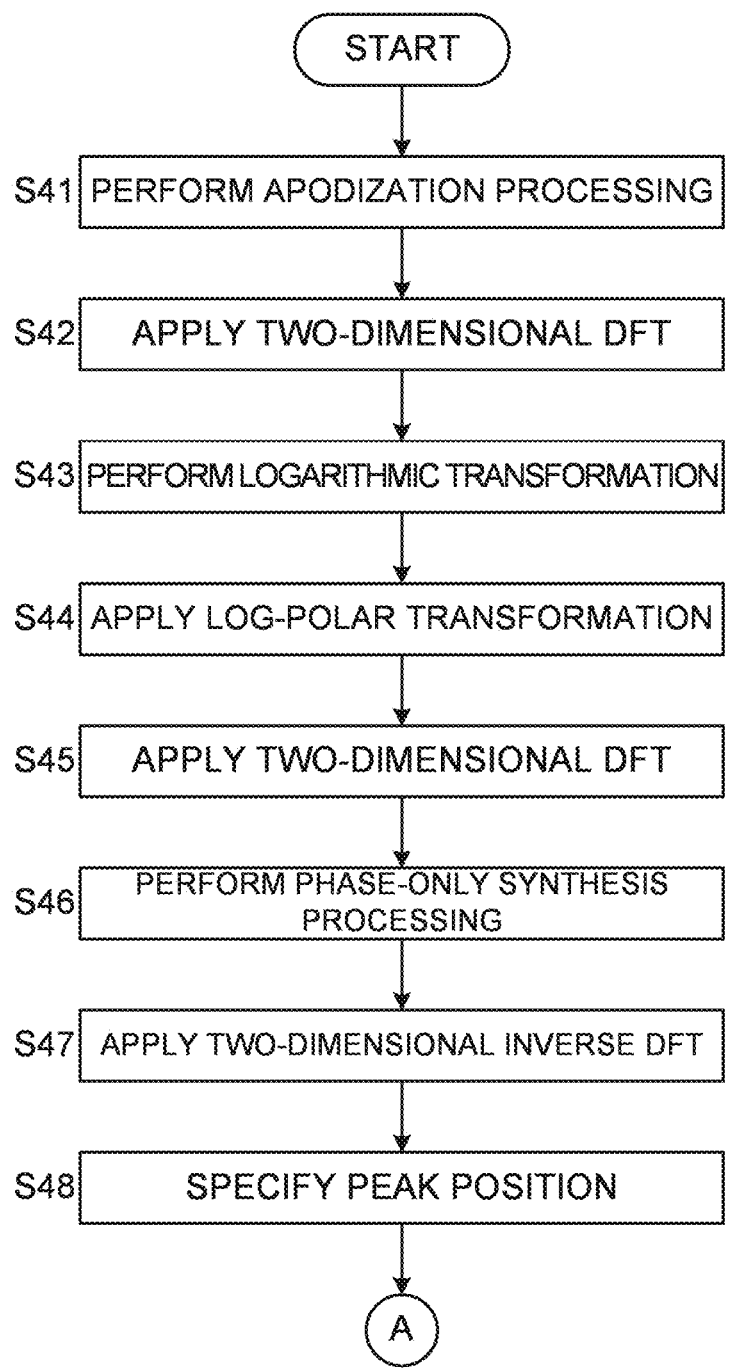
FIG. 12 is a flow chart of an operation example of the ophthalmologic apparatus according to the embodiments.
Figure 13:
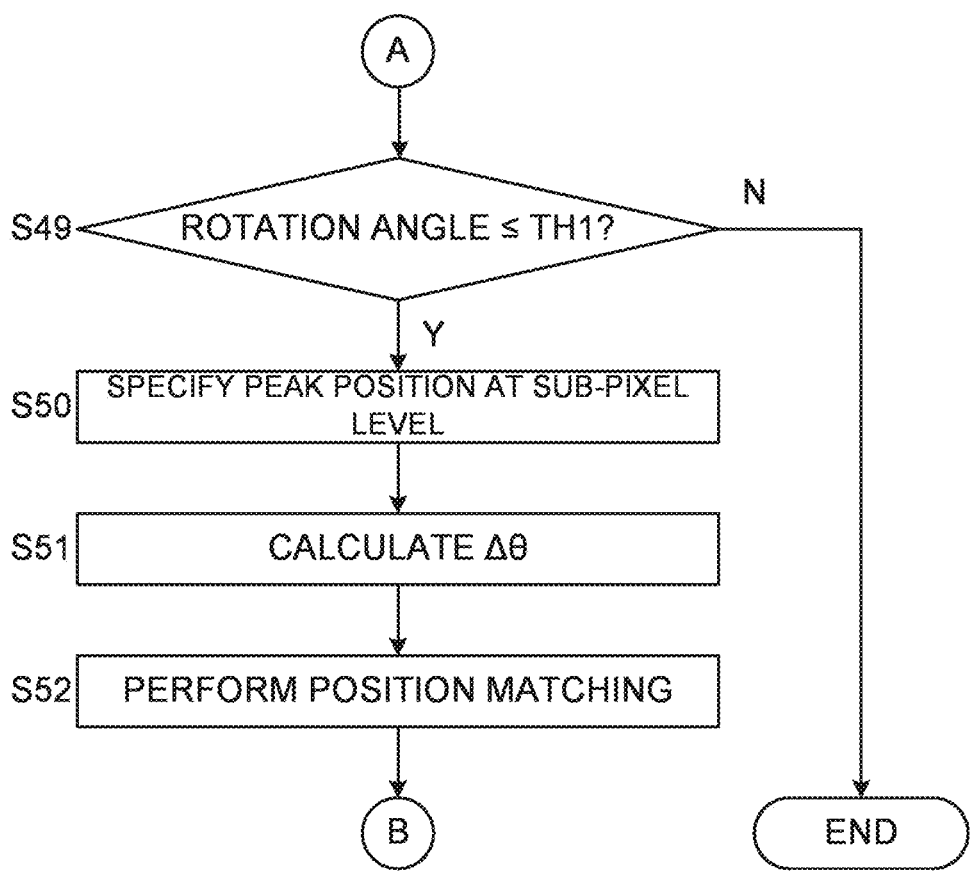
FIG. 13 is a flow chart of an operation example of the ophthalmologic apparatus according to the embodiments.
Figure 14:
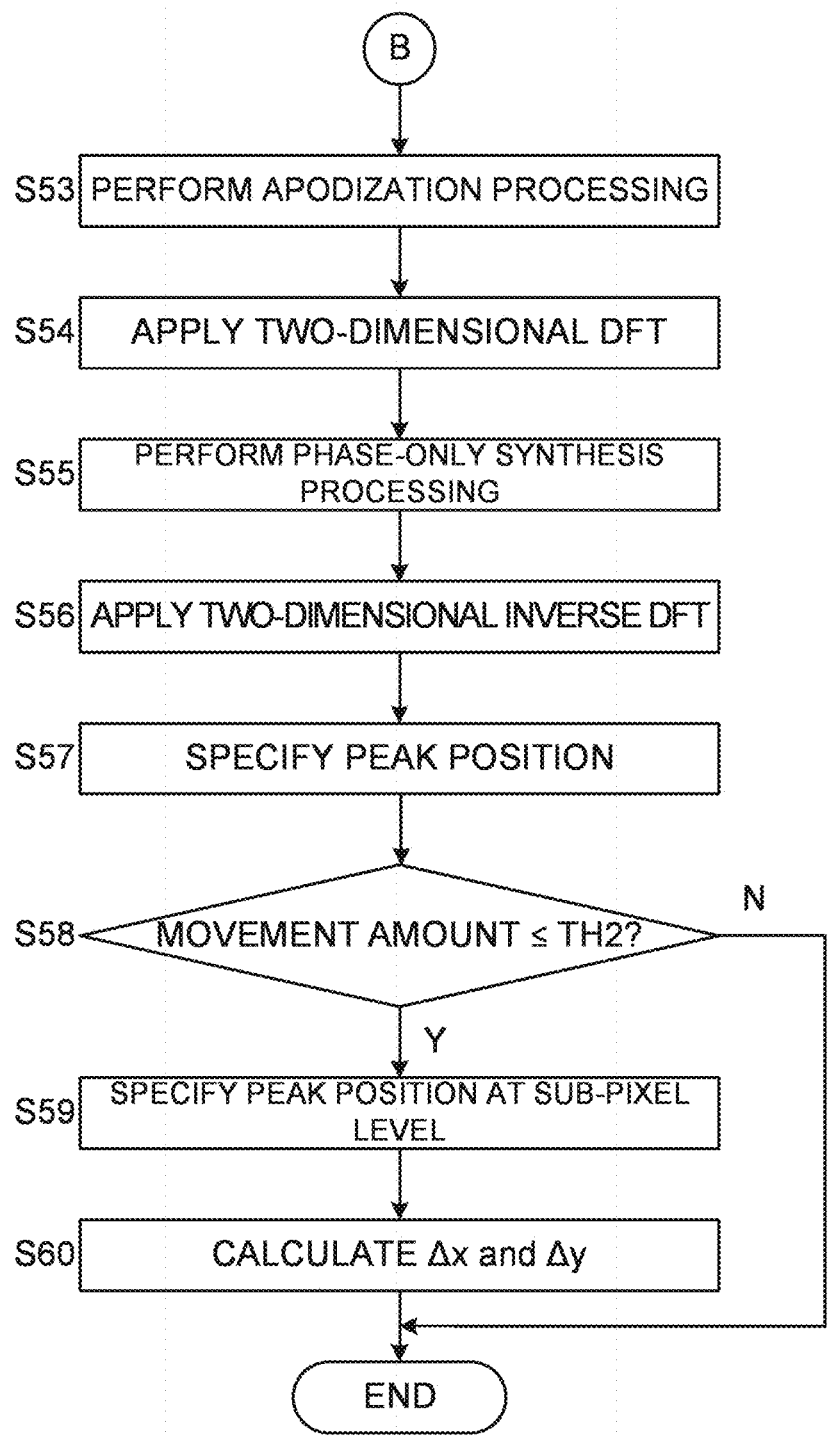
FIG. 14 is a flow chart of an operation example of the ophthalmologic apparatus according to the embodiments.

FIGS. 12 to 14 illustrate examples of flows of the target image processing according to the embodiments. The target image processing includes processing of generating target POC data for the target image, processing of calculating a rotational movement amount and a rotational movement direction, position matching processing, and processing of calculating a parallel movement amount and a parallel movement direction.

(S41: Perform Apodization Processing)

First, the rotational movement processor 221A performs apodization processing on the target image. This processing is performed in the same manner as described in step S21. The apodization processing is performed by, for example, an apodization processor (not illustrated) in the first transformation processor 301 or the rotational movement processor 221A.

(S42: Apply Two-Dimensional DFT)

Next, the first transformation processor 301 applies a two-dimensional DFT to the result of the apodization processing performed on the partial image in step S41.

(S43: Perform Logarithmic Transformation)

Next, the logarithmic transformation unit 302 applies a logarithmic transformation to the processing result of the two-dimensional DFT in step S24. This logarithmic transformation is the same as step S23.

(S44: Apply Log-Polar Transformation)

Next, the polar coordinate transformation unit 303 applies a Log-Polar transformation to the processing result of the logarithmic transformation in step S43. The apodization processing is performed in the same manner as described in step S24.

(S45: Apply Two-Dimensional DFT)

Next, the second transformation processor 304 applies a two-dimensional DFT to the processing result of the Log-Polar transformation in step S44.

(S46: Perform Phase-Only Synthesis Processing)

Next, the first phase-only synthesis unit 305 performs the phase-only synthesis processing according to Equation (3) using the first base POC and the target POC data. Here, the first base POC data is data stored in the storage unit 202 in step S26. The target POC data is data obtained by normalizing the processing result of the two-dimensional DFT in step S45 with the amplitude component. Here, the first base POC data is the base POC data generated for the partial data corresponding to the target image.

(S47: Apply Two-Dimensional IDFT)

Next, the first inverse transformation processor 306 applies a two-dimensional IDFT to the processing result of the phase-only synthesis processing in step S46 according to Equation (4).

(S48: Specify Peak Position)

By specifying a peak position from the processing result of step S47, the radius (a coordinate in the X direction) and the argument (a coordinate in the Y direction) with a high correlation value are specified at the pixel level. Accordingly, the rotational movement processor 221A obtains a peak value of the processing result of step S47, obtains the address of a peak position corresponding to the peak value, and stores it in the storage unit 202.

(S49: Rotation Angle≤TH1?)

The rotational movement processor 221A determines whether or not the rotation angle (absolute value) corresponding to the argument is equal to or less than the first threshold value TH1 based on the address of the peak position stored in the storage unit 202. When it is determined that the rotation angle is not equal to or less than the first threshold value TH1 (S49: N), the rotational movement processor 221A determines it as an error, and terminates a series of processes (END). On the other hand, when it is determined that the rotation angle is equal to or less than the first threshold value TH1 (S49: Y), the processing performed by the rotational movement processor 221A proceeds to step S50.

(S50: Specify Peak Position at Sub-Pixel Level)

When it is determined that the rotation angle is equal to or less than the first threshold value TH1 (S49: Y), the rotational movement processor 221A calculates a correlation value of the phase-only correlation function at the sub-pixel level according to Equation (7). In particular, as disclosed in Japanese Unexamined Patent Application Publication No. 2015-043898, the rotational movement processor 221A 241 obtains a plurality of values of the phase-only correlation function at the sub-pixel level represented by Equation (7) and specifies the argument (the coordinate in the Y direction) with a high correlation value by specifying a peak position. The rotational movement processor 221A obtains the address corresponding to the specified peak value and stores it in the storage unit 202.

(S51: Calculate $\Delta\theta$)

Next, as disclosed in Japanese Unexamined Patent Application Publication No. 2015-043898, the rotational movement processor 221A calculates a rotational movement amount $\Delta\theta$ corresponding to the peak position specified at the sub-pixel level. The rotational movement direction is specified by the sign of $\Delta\theta$.

(S52: Perform Position Matching)

When the rotational movement amount $\Delta\theta$ is calculated, the position matching processor 220B rotates the target image stored in the storage unit 202 by $-\Delta\theta$.

(S53: Perform Apodization Processing)

Subsequently, the parallel movement amount processor 222A calculates a parallel movement amount and a parallel movement direction. That is, the parallel movement processor 222A performs the apodization processing on the target image which has been performed position matching in step S52. This processing is performed by an apodization processor (not illustrated) in the third transformation processor 311 or the parallel movement processor 222A.

(S54: Apply Two-Dimensional DFT)

Next, the third transformation processor 311 applies a two-dimensional DFT to the result of the apodization processing performed on the target image in step S53.

(S55: Perform Phase-Only Synthesis Processing)

Next, the second phase-only synthesis unit 312 performs the phase-only synthesis processing according to Equation (3) using the second base POC and the target POC data. Here, the second POC data is data stored in the storage unit 202 in step S29. The target POC data is data obtained by normalizing the processing result of the two-dimensional DFT in step S54 with the amplitude component.

(S56: Apply Two-Dimensional IDFT)

Next, the second inverse transformation processor 313 applies a two-dimensional IDFT to the processing result of the phase-only synthesis processing according to Equation (4).

(S57: Specify Peak Position)

By specifying a peak position from the processing result of step S59, the coordinate in the X direction and the coordinate in the Y direction corresponding to the correlation value are specified. The parallel movement processor 222A obtains the peak value of the processing result in step S59, obtains the address of a peak position corresponding to the peak value, and stores it in the storage unit 202.

(S58: Movement Amount≤TH2?)

The parallel movement processor 222A determines whether or not, for example, the movement amount (absolute value) in the X direction and the movement amount (absolute value) in the Y direction are equal to or less than the second threshold value TH2 based on the address of the peak position stored in the storage unit 202. When it is determined that the movement amount in the X direction and the movement amount in the Y direction are not equal to or less than the second threshold value TH2 (S58: N), the parallel movement processor 222A determines it as an error, and terminates a series of processes (END). On the other hand, when it is determined that the movement amount in the X direction and the movement amount in the Y direction are equal to or less than the second threshold value TH2 (S58: Y), the processing performed by the parallel movement processor 222A proceeds to step S59.

(S59: Specify Peak Position at Sub-Pixel Level)

When it is determined that the movement amount in the X direction and the movement amount in the Y direction are equal to or less than the second threshold value TH2 (S58: Y), the parallel movement processor 222A calculates a correlation value of the phase-only correlation function at the sub-pixel level according to Equation (7). In particular, as disclosed in Japanese Unexamined Patent Application Publication No. 2015-043898, the parallel movement processor 222A obtains a plurality of values of the phase-only correlation function at the sub-pixel level represented by Equation (7) and specifies the movement amount (the coordinate in the X direction and the coordinate in the Y direction) with a high correlation value by specifying a peak position. The parallel movement processor 222A obtains the address corresponding to the specified peak value and stores it in the storage unit 202.

(S60: Calculate Δx and Δy)

Next, as disclosed in Japanese Unexamined Patent Application Publication No. 2015-043898, the parallel movement processor 222A calculates the parallel movement amounts Δx and Δy corresponding to the peak position specified at the sub-pixel level. The parallel movement direction is specified by the sing of Δx and Δy. With this, a series of processes of the target image processing is completed (END).

The rotational movement amount Δθ, the rotational movement direction, the parallel movement amounts Δx and Δy, and the parallel movement direction calculated as described above are output to the controller 200. The controller 200 (the main controller 201) controls the movement mechanism 100D based on the calculated parallel movement amounts Δx and Δy to move the optical system of apparatus three-dimensionally, thereby performing tracking.

Effects

The ophthalmologic apparatus and the method for controlling the ophthalmologic apparatus according to the embodiments are explained.

An ophthalmologic apparatus according to the embodiments includes SLO system (SLO optical system 130), a projection system (OCT optical system 140 or laser irradiation system), a first image former (base image forming unit 211A), a second image former (target image forming unit 212A), a displacement processor (220A), and a controller (controller 200, main controller 201, tracking controller 201B). The SLO system includes a first optical scanner (optical scanner 136) deflecting first light, and is configured to scan a target eye (subject's eye E) with the first light deflected by the first optical scanner. The projection system includes a second optical scanner (optical scanner 142) deflecting second light (measurement light LS), and is configured to project the second light deflected by the second optical scanner onto the target eye. The first image former is configured to form a first image (base image) of the target eye based on a scan result of a first scan region using the first optical scanner. The second image former is configured to form a second image (target image) of the target eye based on a scan result of a second scan region using the first optical scanner, the second scan region being narrower than the first scan region. The displacement processor is configured to calculate a displacement (displacement amount, displacement direction) between a partial image in the first image and the second image, the partial image corresponding to the second image. The controller is configured to control the second optical scanner based on the displacement calculated by the displacement processor.

According to such a configuration, in the ophthalmologic apparatus including the SLO system and the projection system, the second image is obtained by scanning the second scan region narrower than the first scan region for acquiring the first image, and the second optical scanner in the projection system is controlled based on the displacement between the first image and the second image. Thereby, the second image can be acquired in a short time even when the SLO system is used. Therefore, it becomes possible to follow the eyeball movement during the acquisition of the second image, which is an SLO image, and to perform high-speed tracking control.

Further, in the ophthalmologic apparatus according to the embodiments, the controller may be configured to correct a projection position of the second light based on the displacement, the second light being projected by the projection system.

According to such a configuration, the projection position of the second light projected by the projection system is corrected based on the displacement between the first image and the second image. Thereby, tracking control can be speeded up with simple control.

Further, in the ophthalmologic apparatus according to the embodiments, the second image may be an image corresponding to one of two or more partial images obtained by dividing the first image in a first scan direction (X direction) by the SLO system.

According to such a configuration, the image corresponding to the partial image obtained by dividing the first image in the first scan direction is acquired as the second image. Thereby, tracking control can be improved using an image of wide range while scanning a narrow scan region with simple control.

Further, in the ophthalmologic apparatus according to the embodiments, sizes of the two or more partial images in the first scan direction may be the same.

According to such a configuration, the displacement between the first image and the second image can be obtained with simple control.

Further, in the ophthalmologic apparatus according to the embodiments, the controller may be configured to control the SLO system so as to scan repeatedly while changing a position of the second scan region in the target eye, to cause the second image former to form the second image, to cause the displacement processor to calculate the displacement, and to control the second optical scanner based on the displacement each time scanning of the second scan region is completed.

According to such a configuration, the scanning is performed repeatedly while changing the position of the second scan region. Thereby, it becomes possible to perform tracking control on the target eye with high speed and high precision.

Further, in the ophthalmologic apparatus according to the embodiments, the controller may be configured to repeatedly perform scan of the second scan region by the SLO system so as to scan the entire first scan region.

According to such a configuration, the second optical scanner can be controlled based on the displacement between the second image and various regions in the first image. Thereby, tracking accuracy can be improved.

Further, in the ophthalmologic apparatus according to the embodiments, the displacement processor may be configured to calculate at least one of a parallel movement amount and a parallel movement direction of the target eye, and a rotational movement amount and a rotational movement direction of the target eye by performing phase-only correlation processing on the partial image and the second image.

According to such a configuration, a fine displacement amount between the partial image and the second image can be obtained. Thereby, tracking control can be performed with high precision.

Further, in the ophthalmologic apparatus according to the embodiments, the projection system further may include an OCT system (OCT optical system 140) configured to project, as the second light, measurement light on the basis of OCT light from an OCT light source via the second optical scanner onto the target eye, and to receive interference light (LC) between returning light of the measurement light and reference light (LR) on the basis of the OCT light, and the ophthalmologic apparatus further may include a third image former (OCT image forming unit 210B) configured to form a tomographic image of the target eye based on a light receiving result of the interference light by the OCT system.

According to such a configuration, in the ophthalmologic apparatus including the SLO system and the OCT system, the second image is obtained by scanning the second scan region narrower than the first scan region for acquiring the first image, and the second optical scanner in the projection system is controlled based on the displacement between the first image and the second image. Thereby, the second image can be acquired in a short time even when the SLO system is used. Therefore, it becomes possible to follow the eyeball movement during the acquisition of the second image, which is an SLO image, and to perform high-speed tracking control.

Further, in the ophthalmologic apparatus according to the embodiments, the projection system may include a laser irradiation system configured to irradiate the target eye with laser light from a light source.

According to such a configuration, in the ophthalmologic apparatus including the SLO system and the laser irradiation system, the second image is obtained by scanning the second scan region narrower than the first scan region for acquiring the first image, and the second optical scanner in the projection system is controlled based on the displacement between the first image and the second image. Thereby, the second image can be acquired in a short time even when the SLO system is used. Therefore, it becomes possible to follow the eyeball movement during the acquisition of the second image, which is an SLO image, and to perform high-speed tracking control.

Further, a method for controlling an ophthalmologic apparatus, the ophthalmologic apparatus including: an SLO system including a first optical scanner deflecting first light, and configured to scan a target eye with the first light deflected by the first optical scanner; and a projection system including a second optical scanner deflecting second light, and configured to project the second light deflected by the second optical scanner onto the target eye, may include: a first image forming step of forming a first image of the target eye based on a scan result of a first scan region using the first optical scanner; a second image forming step of forming a second image of the target eye based on a scan result of a second scan region using the first optical scanner, the second scan region being narrower than the first scan region; a displacement processing step of calculating a displacement between a partial image in the first image and the second image, the partial image corresponding to the second image; and a control step of controlling the second optical scanner based on the displacement.

According to such a method, in the ophthalmologic apparatus including the SLO system and the projection system, the second image is obtained by scanning the second scan region narrower than the first scan region for acquiring the first image, and the second optical scanner in the projection system is controlled based on the displacement between the first image and the second image. Thereby, the second image can be acquired in a short time even when the SLO system is used. Therefore, it becomes possible to follow the eyeball movement during the acquisition of the second image, which is an SLO image, and to perform high-speed tracking control.

Further, in the method for controlling the ophthalmologic apparatus according to the embodiments, a projection position of the second light projected by the projection system may be corrected based on the displacement in the control step.

According to such a method, the projection position of the second light projected by the projection system is corrected based on the displacement between the first image and the second image. Thereby, tracking control can be speeded up with simple control.

Further, in the method for controlling the ophthalmologic apparatus according to the embodiments, the SLO system may be controlled so as to scan repeatedly while changing a position of the second scan region with respect to the target eye in the controlling step, and each time scanning of the second region is completed, the second image may be formed in the second image forming step, the displacement may be calculated in the displacement processing step, and the second optical scanner may be controlled based on the displacement in the control step.

According to such a method, the scanning is performed repeatedly while changing the position of the second scan region. Thereby, it becomes possible to perform tracking control on the target eye with high speed and high precision Modification Example The above-described embodiments are merely examples for carrying out the present invention. Those who intend to implement the present invention can apply any modification, omission, addition, or the like within the scope of the gist of the present invention.

In the above embodiments, examples are described in which the configuration of the optical system 100 has the configuration shown in FIG. 1 or FIG. 3; however, they are not so limited. The optical system according to the embodiments may include an optical system for irradiating a laser light on a treatment site in the fundus, an optical system for moving a visual target in a state where the subject's eye is being fixated, or the like.

In the above embodiments, examples are described in which the configuration of the objective lens system 110 has the configuration shown in FIGS. 1 to 3; however, they are not so limited.

The anterior segment photographing system according to the embodiments may include two or more cameras for photographing the anterior segment of the subject's eye E form two or more different directions. In this case, the alignment controller 201A according to the embodiments can perform alignment in the Z direction from parallax obtained based on the photographic images of the anterior segment from two or more different directions using these cameras.

In the above-described embodiments, the case where alignment is performed using the anterior segment image acquired using the anterior segment photographing system 120 has been described. However, the acquired anterior segment image may be displayed on the UI unit 230. Further, the acquired anterior segment image need not be used for alignment.

In some embodiments, a program for causing a computer to execute the method for controlling the ophthalmologic apparatus is provided. Such a program can be stored in any computer-readable recording medium (for example, a non-transitory recording medium). Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus comprising:
   an SLO system including a first optical scanner deflecting first light, and configured to scan a target eye with the first light deflected by the first optical scanner;
   a projection system including a second optical scanner deflecting second light, and configured to project the second light deflected by the second optical scanner onto the target eye;
   a first image former configured to form a first image of the target eye based on a scan result of a first scan region using the first optical scanner;
   a second image former configured to form a second image of the target eye based on a scan result of a second scan region using the first optical scanner, the second scan region being narrower than the first scan region;
   a displacement processor configured to calculate a displacement between a partial image in the first image and the second image, the partial image corresponding to the second image; and
   a controller configured to control the second optical scanner based on the displacement calculated by the displacement processor.

2. The ophthalmologic apparatus according to claim 1, wherein
   the controller is configured to correct a projection position of the second light based on the displacement, the second light being projected by the projection system.

3. The ophthalmologic apparatus according to claim 1, wherein
   the second image is an image corresponding to one of two or more partial images obtained by dividing the first image in a first scan direction by the SLO system.

4. The ophthalmologic apparatus according to claim 3, wherein
   sizes of the two or more partial images in the first scan direction are the same.

5. The ophthalmologic apparatus according to claim 1, wherein
   the controller is configured
   to control the SLO system so as to scan repeatedly while changing a position of the second scan region in the target eye,
   to cause the second image former to form the second image, to cause the displacement processor to calculate the displacement, and to control the second optical scanner based on the displacement, each time scanning of the second scan region is completed.

6. The ophthalmologic apparatus according to claim 5, wherein
   the controller is configured to repeatedly perform scan of the second scan region by the SLO system so as to scan the entire first scan region.

7. The ophthalmologic apparatus according to claim 1, wherein
   the displacement processor is configured to calculate at least one of a parallel movement amount and a parallel movement direction of the target eye, and a rotational movement amount and a rotational movement direction of the target eye by performing phase-only correlation processing on the partial image and the second image.

8. The ophthalmologic apparatus according to claim 1, wherein
   the projection system further comprises an OCT system configured to project, as the second light, measurement light on the basis of OCT light from an OCT light source via the second optical scanner onto the target eye, and to receive interference light between returning light of the measurement light and reference light on the basis of the OCT light, and
   the ophthalmologic apparatus further comprises a third image former configured to form a tomographic image of the target eye based on a light receiving result of the interference light by the OCT system.

9. The ophthalmologic apparatus according to claim 1, wherein the projection system comprises a laser irradiation system configured to irradiate the target eye with laser light from a light source.

10. A method for controlling an ophthalmologic apparatus, the ophthalmologic apparatus comprising:
- an SLO system including a first optical scanner deflecting first light, and configured to scan a target eye with the first light deflected by the first optical scanner; and
- a projection system including a second optical scanner deflecting second light, and configured to project the second light deflected by the second optical scanner onto the target eye, the method comprising:
- a first image forming step of forming a first image of the target eye based on a scan result of a first scan region using the first optical scanner;
- a second image forming step of forming a second image of the target eye based on a scan result of a second scan region using the first optical scanner, the second scan region being narrower than the first scan region;
- a displacement processing step of calculating a displacement between a partial image in the first image and the second image, the partial image corresponding to the second image; and
- a control step of controlling the second optical scanner based on the displacement.

11. The method for controlling the ophthalmologic apparatus according to claim 10, wherein a projection position of the second light projected by the projection system is corrected based on the displacement in the control step.

12. The method for controlling the ophthalmologic apparatus according to claim 10, wherein the SLO system is controlled so as to scan repeatedly while changing a position of the second scan region with respect to the target eye in the controlling step, and each time scanning of the second region is completed, the second image is formed in the second image forming step, the displacement is calculated in the displacement processing step, and the second optical scanner is controlled based on the displacement in the control step.

* * * * *